US012721937B2

(12) United States Patent
Kusters et al.

(10) Patent No.: US 12,721,937 B2
(45) Date of Patent: Sep. 1, 2026

(54) CONFIGURABLE SYSTEM TO AUTOMATE BLOOD COMPONENT MANUFACTURING PROCESSES

(71) Applicant: Fenwal, Inc., Lake Zurich, IL (US)

(72) Inventors: Benjamin E. Kusters, Pleasant Prairie, WI (US); Richard I. Brown, Northbrook, IL (US); Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 1030 days.

(21) Appl. No.: 17/909,799

(22) PCT Filed: Mar. 17, 2021

(86) PCT No.: PCT/US2021/022750

§ 371 (c)(1),
(2) Date: Sep. 7, 2022

(87) PCT Pub. No.: WO2021/194824

PCT Pub. Date: Sep. 30, 2021

(65) Prior Publication Data

US 2024/0226396 A1 Jul. 11, 2024

Related U.S. Application Data

(60) Provisional application No. 63/056,757, filed on Jul. 27, 2020, provisional application No. 63/029,877, (Continued)

(51) Int. Cl.

*A61M 1/36* (2006.01)
*A61M 1/02* (2006.01)

(52) U.S. Cl.

CPC ...... *A61M 1/36224* (2022.05); *A61M 1/0272* (2013.01); *A61M 1/36225* (2022.05);

(Continued)

(58) Field of Classification Search

CPC ........ A61M 1/36224; A61M 1/362266; A61M 1/362265; A61M 1/36225; A61M 1/0272;

(Continued)

(56) References Cited

U.S. PATENT DOCUMENTS

| | | | |
|---|---|---|---|
| 4,157,723 | A | 6/1979 | Granzow et al. |
| 4,753,697 | A | 6/1988 | Shaposka et al. |

(Continued)

FOREIGN PATENT DOCUMENTS

| | | |
|---|---|---|
| EP | 1949923 A2 | 7/2008 |

OTHER PUBLICATIONS

PCT Notification of Transmittal of the International Search Report and the Written Opinion of the ISA for Application No. PCT/US2021/022750 dated Jun. 28, 2021.

*Primary Examiner* — Philip R Wiest
(74) *Attorney, Agent, or Firm* — Cook Alex Ltd.

(57) ABSTRACT

A configurable automated blood component manufacturing system includes a durable hardware component and a single use fluid flow circuit. The hardware component includes a pump station, a centrifuge, and a controller including a touchscreen. The hardware component further includes hangers for suspending containers, a weight scale associated with each hanger, a plurality of tubing clamps, and a cassette nesting module including a plurality of valves and pressure sensors. The fluid flow circuit includes a separation chamber received in the centrifuge, a fluid flow control cassette mounted in the cassette nesting module, and a plurality of containers in fluid communication with the fluid flow cassette. The controller is pre-programmed to automatically operate the system to perform one or more standard blood processing procedures selected by an operator by input to (Continued)

the touchscreen, and is configured to be further programmed by the operator to perform additional blood processing procedures.

19 Claims, 20 Drawing Sheets

Related U.S. Application Data filed on May 26, 2020, provisional application No. 62/994,343, filed on Mar. 25, 2020.

(52) U.S. Cl.
CPC ............................ *A61M 1/362265* (2022.05); *A61M 1/362266* (2022.05); *A61M 1/3643* (2013.01); *A61M 2205/3331* (2013.01); *A61M 2205/505* (2013.01)

(58) Field of Classification Search
CPC ........ A61M 1/3643; A61M 2205/3331; A61M 2205/3334; A61M 2205/505
See application file for complete search history.

(56) References Cited

U.S. PATENT DOCUMENTS

| | | | | |
|---|---|---|---|---|
| 5,156,701 | A | 10/1992 | Spencer et al. | |
| 5,158,630 | A | 10/1992 | Shaposka et al. | |
| 6,849,039 | B2 | 2/2005 | Min et al. | |
| 6,899,666 | B2 * | 5/2005 | Brown | B04B 7/08 210/85 |
| 8,075,468 | B2 * | 12/2011 | Min | A61M 1/3696 494/35 |
| 9,440,396 | B2 | 9/2016 | Kusters et al. | |
| 10,040,247 | B2 | 8/2018 | Schwalm et al. | |
| 10,307,582 | B2 | 6/2019 | Wegener et al. | |
| 2002/0179544 | A1 * | 12/2002 | Johnson | A61M 1/3692 210/806 |
| 2015/0273132 | A1 * | 10/2015 | Ragusa | A61M 1/3633 494/6 |
| 2016/0199563 | A1 * | 7/2016 | Hashimoto | A61M 1/3666 318/490 |
| 2018/0078582 | A1 | 3/2018 | Min et al. | |
| 2018/0154067 | A1 * | 6/2018 | Gibbs | A61M 1/0209 |
| 2019/0201916 | A1 * | 7/2019 | Min | A61M 1/362265 |

* cited by examiner 48
24c
L7
46
24b
24a
L12
62
38d
L11
38a
L6
L8
L5
18
L13
38b
42
L10
44
L1
40c
38c
L9
20
16
40b
60
L4
L3
34
40a
L2
52

48
24c
L7
46
24b
24a
L12
62
38d
L11
38a
L6
L8
L5
18
L13
38b
42
L10
44
L1
40c
38c
L9
20
16
40b
60
L4
L3
34
40a
L2
52

74
L27
70
68
66
72
24c
24b
24a
38b
L17
L20
40c
L26
L24
L25
38d
L29
L28
38c
L19
38a
L23
L18
18
20
16
40b
60
L21
L22
34
40a
52

74
L27
70
68
66
72
24c
24b
24a
38b
L17
L20
40c
L26
L24
L25
38d
L29
L28
38c
L19
38a
L23
L18
18
20
16
40b
60
L21
L22
34
40a
52

CONFIGURABLE SYSTEM TO AUTOMATE BLOOD COMPONENT MANUFACTURING PROCESSES

RELATED APPLICATIONS

This application is a U.S. national stage application of PCT Patent Application Serial No. PCT/US2021/022750, which claims the benefit of U.S. Provisional Application Ser. No. 62/994,343, filed on Mar. 25, 2020; U.S. Provisional Application Ser. No. 63/029,877 filed on May 26, 2020; and U.S. Provisional Application Ser. No. 63/056,757 filed on Jul. 27, 2020, the disclosures of which are hereby incorporated by reference in their entirety.

DESCRIPTION

Technical Field

The present disclosure relates generally to blood and blood component storing, treating and/or processing, and related novel apparatus, systems and methods associated with such storing, treating and/or processing.

Background

It is well known to collect whole blood from donors using manual collection procedures through blood drives, donor visits to blood centers or hospitals and the like. In such procedures, blood is typically collected by simply flowing it from the donor under the force of gravity and venous pressure into a collection container (e.g., a flexible pouch or bag). Although various blood collection instruments may be used to aid or expedite the collection of blood or blood components.

The collection container in manual collection is often part of a larger pre-assembled arrangement of tubing and containers (sometimes called satellite containers) that are used in further processing of the collected whole blood. More specifically, the whole blood is typically first collected in what is called a primary collection container that also contains an anticoagulant, such as but not limited to a solution of sodium citrate, phosphate, and dextrose ("CPD").

After initial collection, it is a common practice to transport the collected whole blood to another facility or location, sometimes called a "back lab," for further processing to separate red blood cells, platelet, and plasma from the whole blood, which may including carrying out additional processes, such as cell washing and plasma cryoprecipitate production and collection. This processing usually entails manually loading the primary collection container and associated tubing and satellite containers into a centrifuge to separate the whole blood into concentrated red cells and platelet-rich or platelet-poor plasma. The separated components may then be expressed from the primary collection container into one or more of the satellite containers, with the red blood cells being combined with an additive or preservative solution pre-filled in one of the satellite containers. After the above steps, the blood components may be again centrifuged, if desired, for example to separate platelets from plasma. The overall process requires multiple large floor centrifuges and fluid expression devices. Because of the multiple operator interactions, the process is labor intensive, time consuming, and subject to human error.

Thus, there have been continuing efforts to automate the apparatus and systems used in the post-collection processing of whole blood, and recently it has been proposed to employ an automated blood component separator for such post-collection processing. The subject matter disclosed herein provides further advances in various aspects of the apparatus, systems and methods that may be employed in whole blood collection and post-collection processing systems by using continuous flow centrifugation in a system that utilizes a programmable controller that is pre-programed to automatically perform selected back lab processes and may also be programmed by the user to meet needs and requirements specific to the user.

SUMMARY

There are several aspects of the present subject matter which may be embodied separately or together in the devices, systems, and methods described and/or claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto or later amended. For purposes of this description and claims, unless otherwise expressly indicated, "blood" is intended to include whole blood and blood components, such as concentrated red cells, plasma, platelets and white cells, whether with or without anticoagulant or additives.

The following summary is to acquaint the reader generally with various potential aspects of the present subject matter, and is non-limiting and non-exclusive with respect to the various possible aspects or combinations of aspects. Additional aspects and features may be found in the detailed description herein and/or in the accompanying figures.

By way of the present disclosure, a configurable automated blood component manufacturing system is provided comprising a durable hardware component and a single use fluid flow circuit. The durable hardware component comprises a pump station with plurality of pumps, a centrifuge mounting station and drive unit; an optical system associated with the centrifuge mounting station and drive unit, a microprocessor-based controller including a touch screen for receiving operator input and displaying procedure parameters, hangers for suspending containers, a weight scale associated with each hanger configured to send a signal to the controller indicative of a weight of a container supported on an associated hanger, a plurality of tubing clamps, and a cassette nesting module including a plurality of valves and pressure sensors. The single use fluid flow circuit comprises a separation chamber configured to be received in the centrifuge mounting station and drive unit, a fluid flow control cassette configured to be mounted in the cassette nesting module, the cassette having external tubing loops engageable with the pumps so that fluid flow through the cassette is controlled by actuation of the pumps and valves, and a plurality of containers in fluid communication with the fluid flow cassette by a tubing segment associated with each container, one or more of the tubing segments being received in one of the tubing clamps. The controller is pre-programmed to automatically operate the system to perform one or more standard blood processing procedures selected by an operator by input to the touch screen, and configured to be further programmed by the operator to perform additional blood processing procedures.

In a second aspect, a blood processing system includes a reusable processing device and a disposable fluid flow circuit. The processing device includes a pump system, a valve system, a centrifuge, and a controller, while the fluid flow circuit includes a processing chamber received by the centrifuge, a red blood cell collection container, a plasma collection container, an additive solution container, and a plurality of conduits fluidly connecting the components of the fluid flow circuit. The controller is configured to execute a blood prime stage in which the pump system conveys whole blood from a blood source to the processing chamber to convey air within the fluid flow circuit into the plasma collection container. The controller then executes an establish separation stage in which the centrifuge separates the whole blood in the processing chamber into plasma and red blood cells and the pump system and the valve system cooperate to convey separated plasma and red blood cells out of the processing chamber, recombine the separated plasma and red blood cells as recombined whole blood, and convey the recombined whole blood into the processing chamber without conveying whole blood from the blood source to the processing chamber. The controller then executes a collection stage in which the pump system conveys whole blood from the blood source to the processing chamber until a total of one unit of whole blood has been conveyed from the blood source to the processing chamber, the centrifuge separates the whole blood in the processing chamber into plasma and red blood cells, and the pump system and the valve system cooperate to convey separated plasma out of the processing chamber and into the plasma collection container, to convey separated red blood cells out of the processing chamber, and to convey additive solution out of the additive solution container, with the separated red blood cells and the additive solution being combined as a mixture and conveyed into the red blood cell collection container. The controller then executes a red blood cell recovery stage in which the pump system and the valve system cooperate to convey air from the plasma collection container into the processing chamber to convey separated red blood cells out of the processing chamber and to convey additive solution out of the additive solution container, with the separated red blood cells and the additive solution continuing to be combined as the mixture and conveyed into the red blood cell collection container. Following the red blood cell recovery stage, the controller executes an additive solution flush stage in which the pump system and the valve system cooperate to convey additive solution from the additive solution container to the red blood cell collection container until a target amount of additive solution has been conveyed into the red blood cell collection container. Following the additive solution flush stage, the controller executes an air evacuation stage in which the pump system and the valve system cooperate to convey air out of the red blood cell collection container.

In another aspect, a method is provided for processing one unit of whole blood into a red blood cell product and a plasma product. The method includes executing a blood prime stage in which whole blood is conveyed from a blood source to a processing chamber of a fluid flow circuit to convey air within the fluid flow circuit into a plasma collection container of the fluid flow circuit. Next, an establish separation stage is executed, in which a centrifuge is operated to separate the whole blood in the processing chamber into plasma and red blood cells, separated plasma and red blood cells are conveyed out of the processing chamber and recombined as recombined whole blood, and the recombined whole blood is conveyed into the processing chamber without conveying whole blood from the blood source to the processing chamber. Following the establish separation stage, a collection stage is executed, in which whole blood is conveyed from the blood source to the processing chamber until a total of one unit of whole blood has been conveyed from the blood source to the processing chamber, the centrifuge is operated to separate the whole blood in the processing chamber into plasma and red blood cells, the separated plasma is conveyed out of the processing chamber and into the plasma collection container, the separated red blood cells are conveyed out of the processing chamber, and an additive solution is conveyed out of an additive solution container of the fluid flow circuit, with the separated red blood cells and the additive solution being combined as a mixture and conveyed into a red blood cell collection container of the fluid flow circuit. After the collection stage, a red blood cell recovery stage is executed, in which air from the plasma collection container is conveyed into the processing chamber to convey separated red blood cells out of the processing chamber and additive solution is conveyed out of the additive solution container, with the separated red blood cells and the additive solution continuing to be combined as the mixture and conveyed into the red blood cell collection container. Next, an additive solution flush stage is executed, in which additive solution is conveyed from the additive solution container to the red blood cell collection container until a target amount of additive solution has been conveyed into the red blood cell collection container. After the additive solution flush stage, an air evacuation stage is executed, in which air is conveyed out of the red blood cell collection container.

In yet another aspect, a blood processing device includes a pump system, a centrifuge, and a controller. The controller is configured to actuate the pump system to convey blood from a blood source into the centrifuge and then actuate the centrifuge to separate the blood in the centrifuge into plasma, red blood cells, and a buffy coat between the separated plasma and the separated red blood cells. The controller then actuates the pump system to convey the separated plasma and the separated red blood cells out of the centrifuge, followed by actuating the pump system to convey air into the centrifuge to convey the buffy coat out of the centrifuge for collection.

In another aspect, a blood processing system includes a reusable processing device and a disposable fluid flow circuit. The processing device includes a pump system, a centrifuge, and a controller, while the fluid flow circuit includes a processing chamber received by the centrifuge, a buffy coat collection container, and a plurality of conduits fluidly connecting the components of the fluid flow circuit. The controller is configured to actuate the pump system to convey blood from a blood source into the processing chamber, then actuate the centrifuge to separate the blood in the processing chamber into plasma, red blood cells, and a buffy coat between the separated plasma and the separated red blood cells. Next, the controller actuates the pump system to convey the separated plasma and the separated red blood cells out of the processing chamber, followed by actuating the pump system to convey air into the processing chamber to convey the buffy coat out of the processing chamber and into the buffy coat collection container.

In yet another aspect, a method for collecting a buffy coat product includes conveying blood from a blood source into a centrifuge, which separates the blood in the centrifuge into plasma, red blood cells, and a buffy coat between the separated plasma and the separated red blood cells. The separated plasma and the separated red blood cells are conveyed out of the centrifuge, followed by air being conveyed into the centrifuge to convey the buffy coat out of the centrifuge for collection.

In another aspect, a blood processing system includes a reusable processing device and a disposable fluid flow circuit. The processing device includes a pump system, a valve system, a centrifuge, and a controller. The fluid flow circuit includes a processing chamber received by the centrifuge, a red blood cell source container, a washed red blood cell container, a waste container, and a plurality of conduits fluidly connecting the components of the fluid flow circuit. The controller is configured to execute a priming stage in which the pump system and the valve system cooperate to convey air within the fluid flow circuit into the waste container. The controller then executes a washing stage in which the pump system and the valve system cooperate to convey red blood cells from the red blood cell source container to the processing chamber, the centrifuge separates the red blood cells into a supernatant and washed red blood cells, and the pump system and the valve system cooperate to convey the supernatant out of the processing chamber and into the waste container and to convey the washed red blood cells out of the processing chamber and into the washed red blood cell container. The controller then executes a red blood cell recovery stage in which the pump system and the valve system cooperate to convey air from the waste container into the processing chamber to convey washed red blood cells out of the processing chamber and into the washed red blood cell container, followed by executing an air evacuation stage in which the pump system and the valve system cooperate to convey air out of the washed red blood cell container.

In yet another aspect, a method is provided for washing red blood cells. The method includes executing a priming stage in which air within a fluid flow circuit is conveyed into a waste container of the fluid flow circuit. This is followed by a washing stage in which red blood cells are conveyed to a processing chamber of the fluid flow circuit, the centrifuge separates the red blood cells into a supernatant and washed red blood cells, the supernatant is conveyed out of the processing chamber and into the waste container of the fluid flow circuit and the washed red blood cells are conveyed out of the processing chamber and into a washed red blood cell container of the fluid flow circuit. Next, a red blood cell recovery stage is executed, with air from the waste container being conveyed into the processing chamber to convey washed red blood cells out of the processing chamber and into the washed red blood cell container, followed by an air evacuation stage in which air is conveyed out of the washed red blood cell container.

These and other aspects of the present subject matter are set forth in the following detailed description of the accompanying drawings.

DETAILED DESCRIPTION OF THE ILLUSTRATED EMBODIMENTS

The embodiments disclosed herein are for the purpose of providing an exemplary description of the present subject matter. They are, however, only exemplary and not exclusive, and the present subject matter may be embodied in various forms. Therefore, specific details disclosed herein are not to be interpreted as limiting the subject matter as defined in the accompanying claims.

Figure 1:
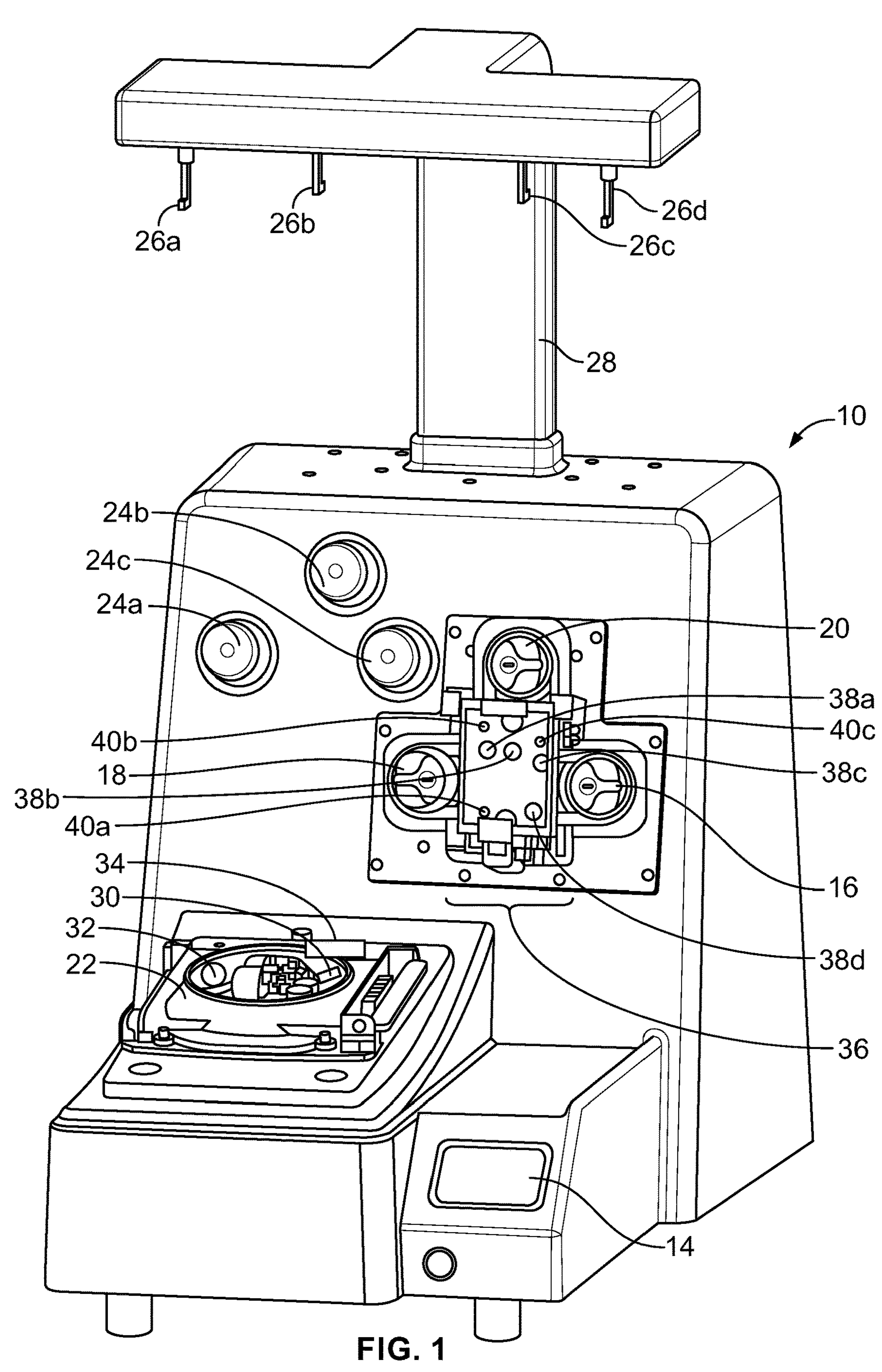
FIG. 1 is a perspective view of an exemplary reusable hardware component of a blood processing system which is configured to receive a disposable fluid flow circuit.
Figure 2:
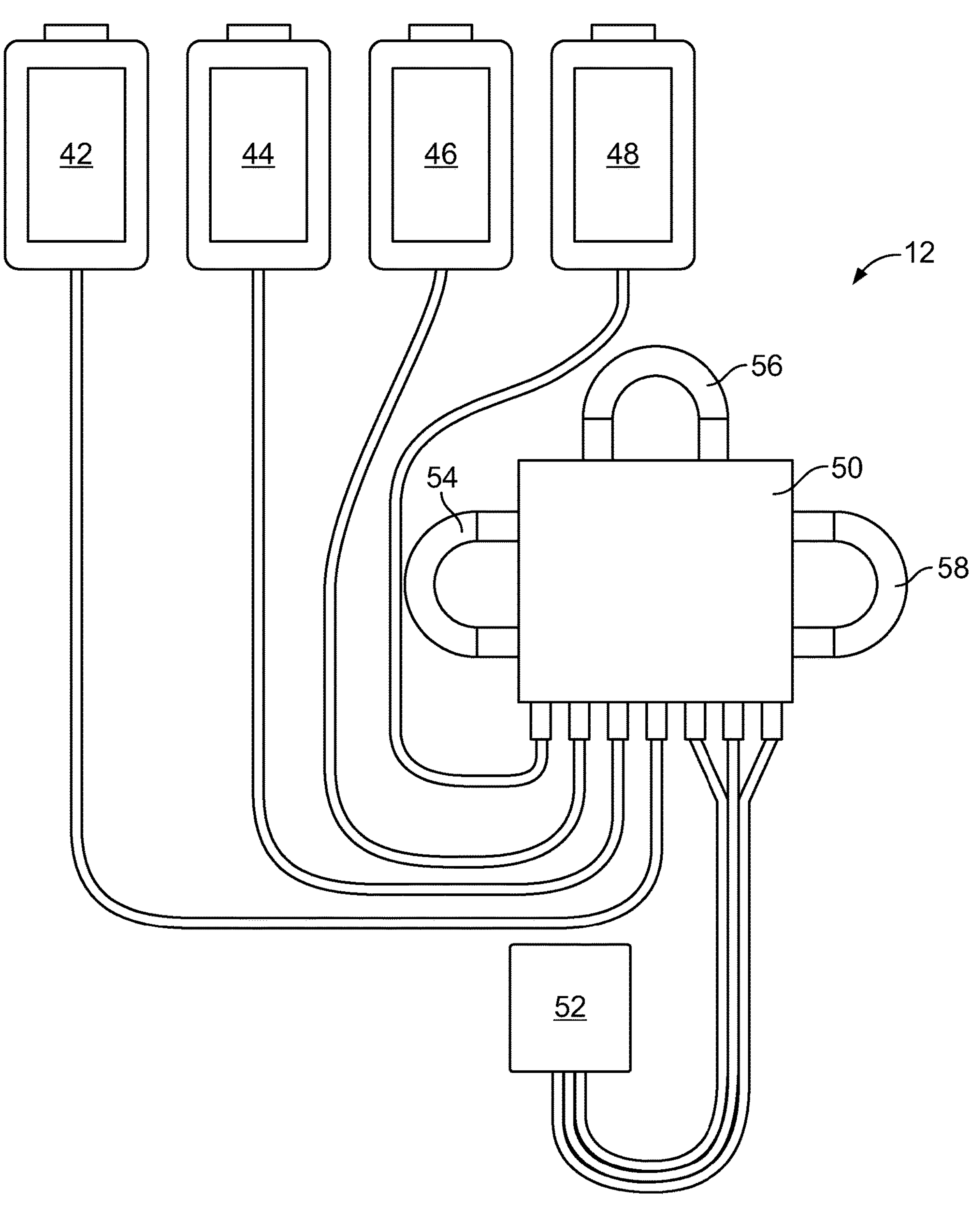
FIG. 2 is a plan view of an exemplary disposable fluid flow circuit for use in combination with the durable hardware component of FIG. 1.

FIG. 1 depicts a reusable or durable hardware component or processing device of a configurable, automated blood processing system or blood component manufacturing system, generally designated 10, while FIG. 2 depicts a disposable or single use fluid flow circuit, generally designated 12, to be used in combination with the processing device 10 for processing collected whole blood. The illustrated processing device 10 includes associated pumps, valves, sensors, displays, and other apparatus for configuring and controlling flow of fluid through the fluid flow circuit 12, described in greater detail below. The blood processing system may be directed by a controller integral with the processing device 10 that includes a programmable microprocessor to automatically control the operation of the pumps, valves, sensors, etc. The processing device 10 may also include wireless communication capabilities to enable the transfer of data from the processing device 10 to the quality management systems of the operator.

More specifically, the illustrated processing device 10 includes a user input and output touchscreen 14, a pump station or system including a first pump 16 (for pumping, e.g., whole blood), a second pump 18 (for pumping, e.g., plasma) and a third pump 20 (for pumping, e.g., additive solution), a centrifuge mounting station and drive unit 22 (which may be referred to herein as a "centrifuge"), and clamps 24*a-c*. The touchscreen 14 enables user interaction with the processing device 10, as well as the monitoring of procedure parameters, such as flow rates, container weights, pressures, etc. The pumps 16, 18, and 20 (collectively referred to herein as being part of a "pump system" of the processing device 10) are illustrated as peristaltic pumps capable of receiving tubing or conduits and moving fluid at various rates through the associated conduit dependent upon the procedure being performed. An exemplary centrifuge mounting station/drive unit is seen in U.S. Pat. No. 8,075,468 (with reference to FIGS. 26-28), which is hereby incorporated herein by reference. The clamps 24*a-c* (collectively referred to herein as being part of the "valve system" of the processing device 10) are capable of opening and closing fluid paths through the tubing or conduits and may incorporate RF sealers in order to complete a heat seal of the tubing or conduit placed in the clamp to seal the tubing or conduit leading to a product container upon completion of a procedure.

Sterile connection/docking devices may also be incorporated into one or more of the clamps 24*a-c*. The sterile connection devices may employ any of several different operating principles. For example, known sterile connection devices and systems include radiant energy systems that melt facing membranes of fluid flow conduits, as in U.S. Pat. No. 4,157,723; heated wafer systems that employ wafers for cutting and heat bonding or splicing tubing segments together while the ends remain molten or semi-molten, such as in U.S. Pat. Nos. 4,753,697; 5,158,630; and 5,156,701; and systems employing removable closure films or webs sealed to the ends of tubing segments as described, for example, in U.S. Pat. No. 10,307,582. Alternatively, sterile connections may be formed by compressing or pinching a sealed tubing segment, heating and severing the sealed end, and joining the tubing to a similarly treated tubing segment as in, for example, U.S. Pat. Nos. 10,040,247 and 9,440,396. All of the above-identified patents are incorporated by reference in their entirety. Sterile connection devices based on other operating principles may also be employed without departing from the scope of the present disclosure.

The processing device 10 also includes hangers 26*a-d* (which may each be associated with a weight scale) for suspending the various containers of the disposable fluid circuit 12. The hangers 26*a-d* are preferably mounted to a support 28, which is vertically translatable to improve the transportability of the processing device 10. An optical system comprising a laser 30 and a photodetector 32 is associated with the centrifuge 22 for determining and controlling the location of an interface between separated blood components within the centrifuge 22. An exemplary optical system is shown in U.S. Patent Application Publication No. 2019/0201916, which is hereby incorporated herein by reference. An optical sensor 34 is also provided to optically monitor one or more conduits leading into or out of the centrifuge 22.

The face of the processing device 10 includes a nesting module 36 for seating a flow control cassette 50 (FIG. 2) of the fluid flow circuit 12 (described in greater detail below). The cassette nesting module 36 is configured to receive various disposable cassette designs so that the system may be used to perform different types of procedures. Embedded within the illustrated cassette nesting module 36 are four valves 38*a-d* (collectively referred to herein as being part of the "valve system" of the processing device 10) for opening and closing fluid flow paths within the flow control cassette 50, and three pressure sensors 40*a-c* capable of measuring the pressure at various locations of the fluid flow circuit 12.

With reference to FIG. 2, the illustrated fluid flow circuit 12 includes a plurality of containers 42, 44, 46, and 48, with a flow control cassette 50 and a processing/separation chamber 52 that is configured to be received in the centrifuge 22, all of which are interconnected by conduits or tubing segments, so as to permit continuous flow centrifugation. The flow control cassette 50 routes the fluid flow through three tubing loops 54, 56, 58, with each loop being positioned to engage a particular one of the pumps 16, 18, 20. The conduits or tubing may extend through the cassette 50, or the cassette 50 may have pre-formed fluid flow paths that direct the fluid flow.

In the fluid flow circuit 12 shown in FIG. 2, container 42 may be pre-filled with additive solution, container 44 may be filled with whole blood and connected to the fluid flow circuit 12 at the time of use, container 46 may be an empty container for the receipt of red blood cells separated from the whole blood, and container 48 may be an empty container for the receipt of plasma separated from the whole blood. While FIG. 2 shows a whole blood container 44 (configured as a blood pack unit, for example) as a blood source, it is within the scope of the present disclosure for the blood source to be a living donor, as will be described in greater detail herein. The fluid flow circuit may optionally include an air trap 60 (FIG. 3) through which the whole blood is flowed prior to entering the separation chamber and/or a leukoreduction filter 62 through which the red blood cells are flowed prior to entering the red blood cell collection container 46.

The processing chamber 52 may be pre-formed in a desired shape and configuration by injection molding from a rigid plastic material, as shown and described in U.S. Pat. No. 6,849,039, which is hereby incorporated herein by reference. The specific geometry of the processing chamber 52 may vary depending on the elements to be separated, and the present disclosure is not limited to the use of any specific chamber design. For example, it is within the scope of the present disclosure for the processing chamber 52 to be configured formed of a generally flexible material, rather than a generally rigid material. When the processing chamber 52 is formed of a generally flexible material, it relies upon the centrifuge 22 to define a shape of the processing chamber 52. An exemplary processing chamber formed of a flexible material and an associated centrifuge are described in U.S. Pat. No. 6,899,666, which is hereby incorporated herein by reference.

In keeping with the disclosure, the controller of the processing device 10 is pre-programmed to automatically operate the system to perform one or more standard blood processing procedures selected by an operator by input to the touchscreen 14, and configured to be further programmed by the operator to perform additional blood processing procedures. The controller may be pre-programmed to substantially automate a wide variety of procedures, including, but not limited to: red blood cell and plasma production from a single unit of whole blood (as will be described in greater detail herein), buffy coat pooling, buffy coat separation into a platelet product (as described in U.S. Patent Application Publication No. 2018/0078582, which is hereby incorporated herein by reference), glycerol addition to red blood cells, red blood cell washing, platelet washing, and cryoprecipitate pooling and separation.

The pre-programmed blood processing procedures operate the system at pre-set settings for flow rates and centrifugation forces, and the programmable controller may be further configured to receive input from the operator as to one or more of flow rates and centrifugation forces for the standard blood processing procedure to override the pre-programmed settings.

In addition, the programmable controller is configured to receive input from the operator through the touchscreen 14 for operating the system to perform a non-standard blood processing procedure. More particularly, the programmable controller may be configured to receive input for settings for the non-standard blood processing procedure, including flow rates and centrifugation forces.

Red Blood Cell and Plasma Product Collection

Figures 3, 4:
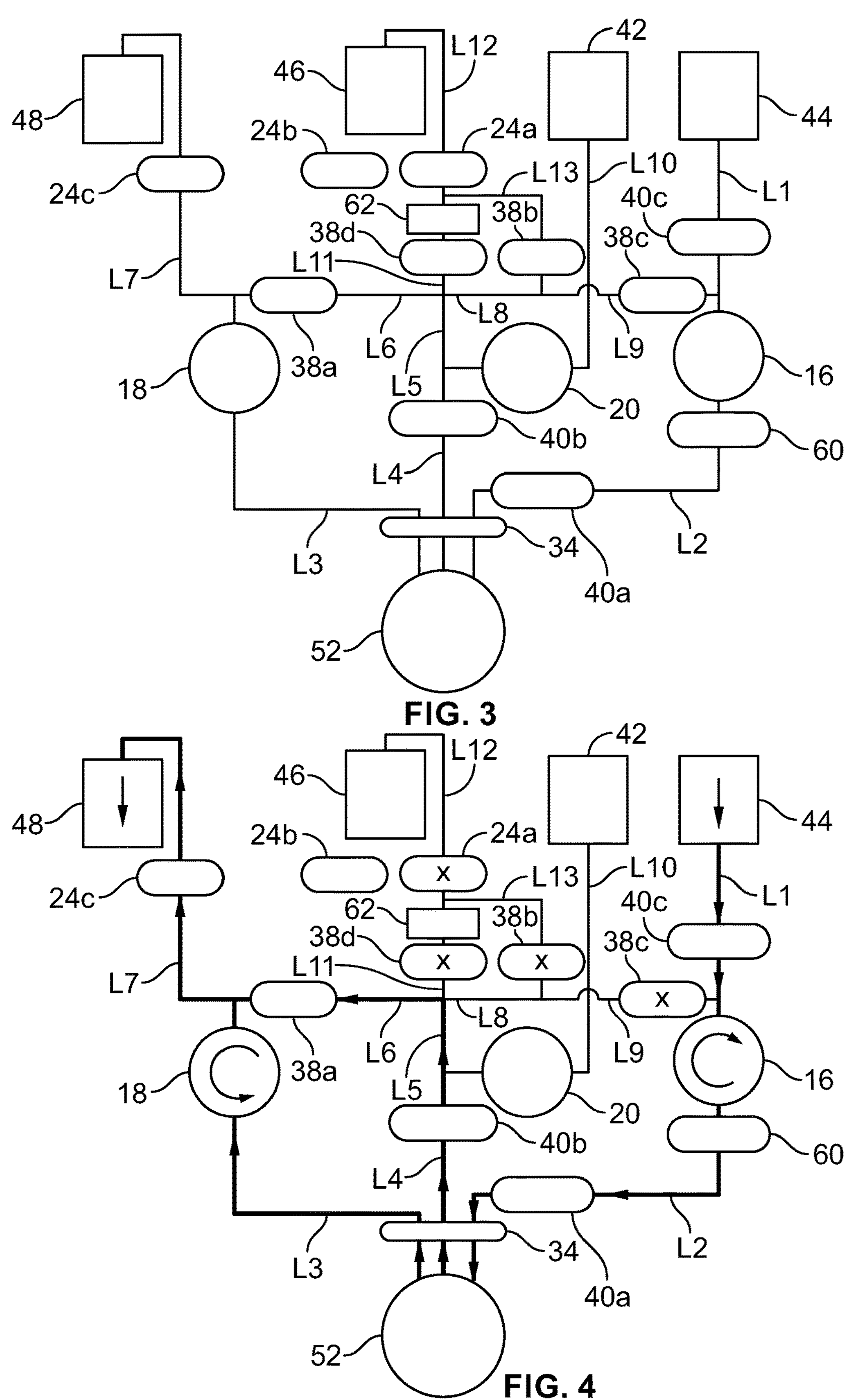
FIG. 3 is a schematic view of the fluid flow circuit of FIG. 2 mounted to the processing device of FIG. 1 to complete a blood processing system according to an aspect of the present disclosure.
FIG. 4 is a schematic view of the blood processing system of FIG. 3 executing a "blood prime" stage of an exemplary blood processing procedure.

In an exemplary procedure, the processing device 10 and the fluid flow circuit 12 may be used in combination to process a unit of whole blood into a red blood cell product and a plasma product. FIG. 3 is a schematic illustration of the fluid flow circuit 12 mounted to the processing device 10, with selected components of the fluid flow circuit 12 and selected components of the processing device 10 being shown. FIGS. 4-13 show different stages of an exemplary procedure. As shown in FIGS. 3-13, one of the clamps 24*b* is not used in producing the red blood cell and plasma products (but would be used in other procedures, as will be described herein), while the other illustrated components of the processing device 10 are employed.

In an initial stage, which is referred to herein as a "blood prime" stage and shown in FIG. 4, selected components of the fluid flow circuit 12 are primed using blood from a blood source. This is in contrast to typical apheresis devices, which employ a separately provided fluid (e.g., anticoagulant or saline) to prime a fluid flow circuit. The blood source is shown in FIG. 4 as the whole blood container 44, but may alternatively be a living donor. Thus, it should be understood that the term "whole blood" may refer to blood that either includes or omits an anticoagulant fluid.

During the blood prime stage, whole blood is drawn into the fluid flow circuit 12 from the blood source (the whole blood container 44 in the embodiment of FIG. 4) via line L1 by operation of the first pump 16 (which may be referred to as the "whole blood pump"). Valve 38*c* is closed, which directs the blood through pressure sensor 40*c* and into line L2. The blood passes through air trap 60, pressure sensor 40*a* (which measures the pressure of the processing chamber 52), and optical sensor 34 before flowing into the processing chamber 52, which is positioned within the centrifuge 22 of the processing device 10.

The centrifuge 22 may be stationary during the blood prime stage or may instead be controlled by the controller of the processing device 10 to spin at a low rotation rate (e.g., on the order of approximately 1,000-2,000 rpm). It may be advantageous for the centrifuge 22 to rotate during the blood prime stage in order to create enough g-force to ensure that the air in the processing chamber 52 (which includes air already present in the processing chamber 52, along with air moved into the processing chamber 52 from lines L1 and/or L2 by the flow of blood) is forced towards the low-g (radially inner) wall of the processing chamber 52. Higher centrifuge rotation rates, such as 4,500 rpm (which is required for steady state separation, as will be described) may be undesirable as air blocks (in which air gets stuck and cannot be forced out of the processing chamber 52, causing pressure to rise) are more likely at higher g-forces.

The blood entering the processing chamber 52 will move towards the high-g (radially outer) wall of the processing chamber 52, displacing air towards the low-g wall. A plasma outlet port of the processing chamber 52 is associated with the low-g wall of the processing chamber 52, such that most of the air will exit the processing chamber 52 via the plasma outlet port and associated line L3, although some air may also exit the processing chamber 52 via a red blood cell outlet port associated with the high-g wall of the processing chamber 52.

Valves 38*b* and 38*d* are closed, while the second pump 18 (which may be referred to as the "plasma pump") is active and the third pump 20 (which may be referred to as the "additive pump") is inactive. Such an arrangement will direct the air exiting the processing chamber 52 via the red blood cell outlet port through associated line L4 and pressure sensor 40*b*, into line L5 and then into line L6. Valve 38*a* is open, such that the air flowing through line L6 will meet up with the air flowing through line L3 (i.e., the air that exits the processing chamber 52 via the plasma outlet port). The combined air will flow through line L7 and open clamp 24*c*, into the plasma collection container 48. It should be understood that, in FIGS. 4-12, arrows on the containers represent the direction of fluid flow between the container and the conduit connected to the container. For example, line L7 is shown as being connected to the top of the plasma collection container 48, such that a downward arrow (as in FIG. 4) represents downward fluid flow into the plasma collection container 48. In contrast, line L1 is shown as being connected to the bottom of the whole blood container 44, such that a downward arrow (as in FIG. 4) represents downward fluid flow out of the whole blood container 44.

The flow of air out of the processing chamber 52 via either outlet port is monitored by the optical sensor 34, which is capable of determining the optical density of the fluid flowing through the monitored lines and discerning between air and a non-air fluid in lines L3 and L4. When a non-air fluid is detected in both lines L3 and L4, the controller of the processing device 10 will end the blood prime stage and move on to the next stage of the procedure. The amount of blood drawn into the fluid flow circuit 12 from the blood source during the blood prime stage will vary depending on a number of factors (e.g., the amount of air in the fluid flow circuit 12), but may be on the order of approximately 50 to 100 mL. The blood prime stage may take on the order of one to two minutes.

The next stage (shown in FIG. 5) is referred to herein as the "establish separation" stage. Once non-air fluid has been detected in lines L3 and L4, the rotational speed of the centrifuge 22 will be increased to a rate that is sufficient to separate blood into packed red blood cells and platelet-poor plasma (which may be in the range of approximately 4,500 to 5,500 rpm, for example). To produce a plasma product that is low in platelets, it may be advantageous for the processing chamber 52 to be configured with a plasma outlet port that is spaced from and positioned downstream of the blood inlet port, rather than being positioned adjacent to the blood inlet port. Such a configuration allows the platelets to settle down into a distinct layer between the plasma and the red blood cells (commonly referred to as a "buffy coat") before the plasma is removed from the processing chamber 52, thus allowing the separated plasma to be platelet-depleted. As for the whole blood pump 16, it continues to operate, but no additional blood is drawn into the fluid flow circuit 12 from the blood source during the establish separation stage (as will be described).

As the blood source includes (in the case of a whole blood container) or provides (in the case of a living donor) only a single unit of whole blood (approximately 500 mL), the system must work with a finite fluid volume. To avoid product loss or quality issues, the plasma and red blood cells initially separated from the blood in the processing chamber 52 and removed from the processing chamber 52 are not directed to their respective collection containers, but are instead mixed together to form recombined whole blood and recirculated back into the processing chamber 52.

More particularly, during the establish separation stage, separated plasma will exit the processing chamber 52 via the plasma outlet port and associated line L3. Clamp 24*c* is closed during this stage, while valve 38*a* remains open, which directs the plasma from line L3 into line L6. Separated red blood cells exit the processing chamber 52 via the red blood cell outlet port and associated line L4. In the illustrated embodiment, there is no pump associated with line L4, such that the red blood cells exit the processing chamber 52 at a rate that is equal to the difference between the rate of the whole blood pump 16 and the rate of the plasma pump 18. In alternative embodiments, there may be a pump associated with the red blood cell outlet line instead of the plasma outlet line or a first pump associated with the plasma outlet line and a second pump associated with the red blood cell outlet line.

The additive pump 20 is inactive during this stage, thereby directing the red blood cells from line L4 into line L5. The plasma flowing through line L6 is mixed with the red blood cells flowing through line L5 at a junction of the two lines L5 and L6 to form recombined whole blood. Valve 38*d* is closed, which directs the recombined whole blood into line L8. Valve 38*b* is also closed, which directs the recombined whole blood from line L8 into line L9 and through open valve 38*c*. The whole blood pump 16 draws the recombined whole blood into line L2 from line L9 (rather than drawing additional blood into the fluid flow circuit 12 from the blood source), with the recombined blood passing through air trap 60, pressure sensor 40*a*, and optical sensor 34 before flowing back into the processing chamber 52, where it is again separated into plasma and red blood cells.

The establish separation stage continues until steady state separation has been achieved, which may take on the order of approximately one to two minutes. As used herein, the phrase "steady state separation" refers to a state in which blood is separated into its constituents in the processing chamber 52, with the radial position of the interface between separated components within the processing chamber 52 being at least substantially maintained (rather than moving radially inwardly or outwardly). The position of the interface may be determined and controlled according to any suitable approach, including using an interface detector of the type described in U.S. Patent Application Publication No. 2019/0201916.

Preferably, steady state separation is achieved with the interface between separated components within the processing chamber 52 at a target location. The target location may correspond to the location of the interface at which separation efficiency is optimized, with the precise location varying depending on a number of factors (e.g., the hematocrit of the whole blood). However, in an exemplary embodiment, the target location of the interface may be the position of the interface when approximately 52% of the thickness or width (in a radial direction) of the channel defined by the processing chamber 52 is occupied by red blood cells. In the illustrated embodiment, the position of the interface within the processing chamber 52 may be adjusted by changing the flow rate of the plasma pump 18, with the flow rate being increased to draw more separated plasma out of the processing chamber 52 (which decreases the thickness of the plasma layer within the processing chamber 52) and move the interface toward the low-g wall or decreased to draw less plasma out of the processing chamber 52 (which increases the thickness of the plasma layer within the processing chamber 52) and move the interface toward the high-g wall.

In an exemplary procedure, the controller of the processing device 10 will control the whole blood pump 16 to operate at a constant rate, with the plasma pump 18 initially operating at the same rate, which will quickly increase the thickness of the red blood cell layer within the processing chamber 52 and move the interface toward the low-g wall. The rate of the plasma pump 18 is gradually decreased as the thickness of the red blood cell layer increases and the location of the interface approaches the target location. As described above, the target location of the interface may depend upon the hematocrit of the whole blood, meaning that the rate of the plasma pump 18 (which controls the position of the interface) may also depend on the hematocrit of the whole blood. In one embodiment, this relationship may be expressed as follows:

Theoretical plasma pump rate=whole blood pump rate−((whole blood hematocrit*whole blood pump rate)/hematocrit of separated red blood cells) [Equation 1]

The hematocrit of the whole blood may be measured before the procedure begins or by the optical sensor 34 during the procedure, while the hematocrit of the separated red blood cells may be determined during the procedure by the optical sensor 34 monitoring line L4. In practice, the plasma pump rate will typically not remain at the theoretical rate once steady state separation has been achieved, with the interface at the target location, but rather the plasma pump rate will instead tend to "flutter" around the theoretical rate.

Figures 5, 6:
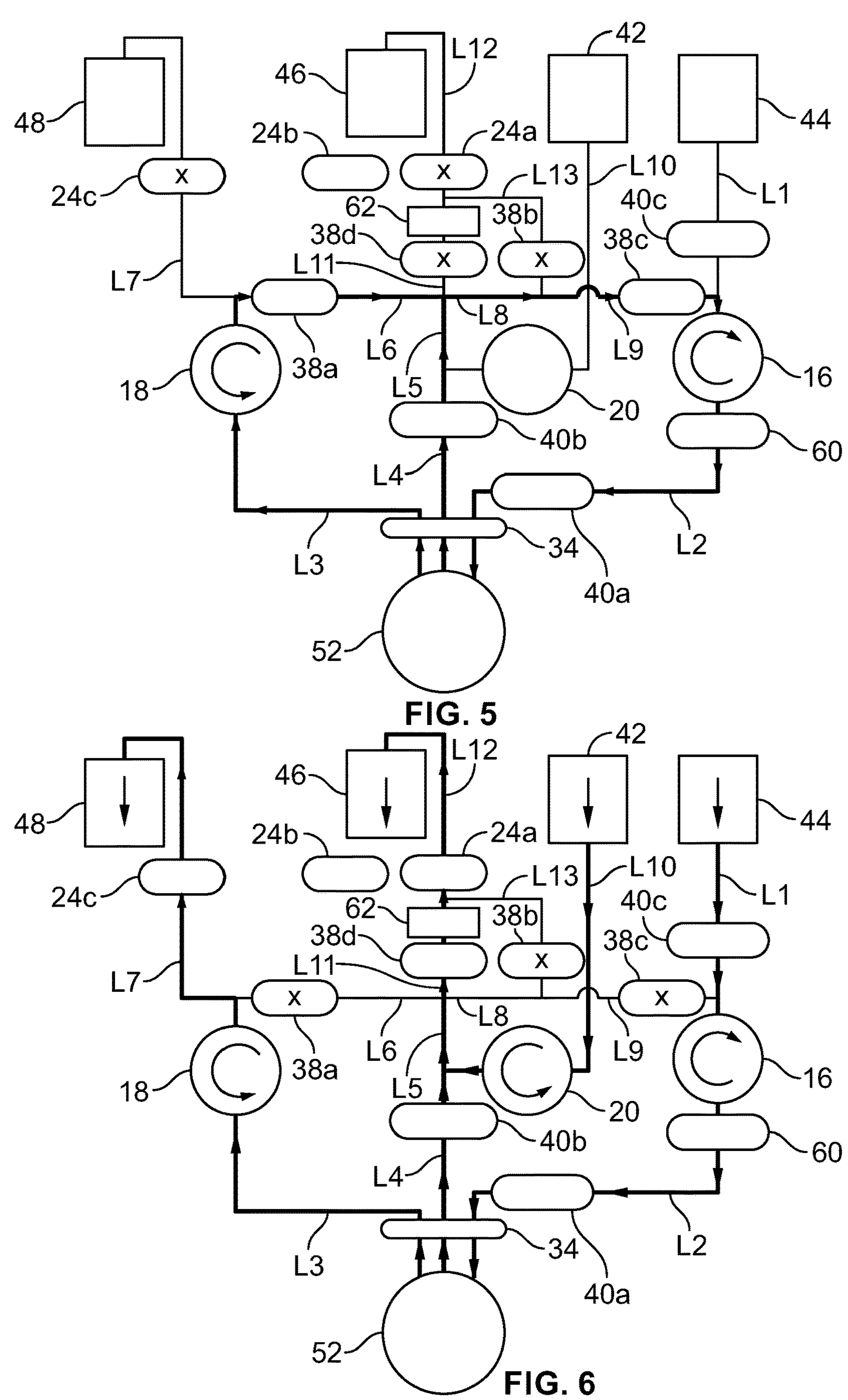
FIG. 5 is a schematic view of the blood processing system of FIG. 3 executing an "establish separation" stage of an exemplary blood processing procedure.
FIG. 6 is a schematic view of the blood processing system of FIG. 3 executing a "collection" stage of an exemplary blood processing procedure, with separated red blood cells being leukoreduced before collection.

Regardless of the particular manner in which the controller of the processing device 10 executes the establish separation stage and arrives at steady state separation, once steady state separation has been established, the controller ends the establish separation stage and advances the procedure to a "collection" stage, which is illustrated in FIG. 6. At the beginning of the collection stage, the centrifuge 22, the whole blood pump 16, and the plasma pump 18 all continue operating at the same rates at which they were operating at the end of the establish separation stage. The valve system of the processing device 10, however, is adjusted to direct the separated plasma and red blood cells to their respective collection containers (rather than recombining them and recirculating them through the centrifuge 22), while causing additional blood to be drawn into the fluid flow circuit 12 from the blood source until a total of one unit of whole blood has been drawn into the fluid flow circuit 12.

More particularly, during the collection stage, valve 38*c* is closed, which causes the whole blood pump 16 to draw additional blood into line L1 from the blood source (which is the whole blood container 44 in the illustrated embodiment, but may be a living donor). The whole blood pump 16 draws the blood from the blood source into line L2 from line L1, with the blood passing through air trap 60, pressure sensor 40*a*, and optical sensor 34 before flowing into the processing chamber 52, where it is separated into plasma and red blood cells. Most of the platelets of the whole blood will remain in the processing chamber 52, along with some white blood cell populations (much as mononuclear cells), while larger white blood cells, such as granulocytes, may exit with the packed red blood cells.

The separated plasma exits the processing chamber 52 via the plasma outlet port and associated line L3. Valve 38*a* is closed, which directs the plasma from line L3 into line L7, through open clamp 24*c*, and into the plasma collection container 48.

Figures 7, 8:
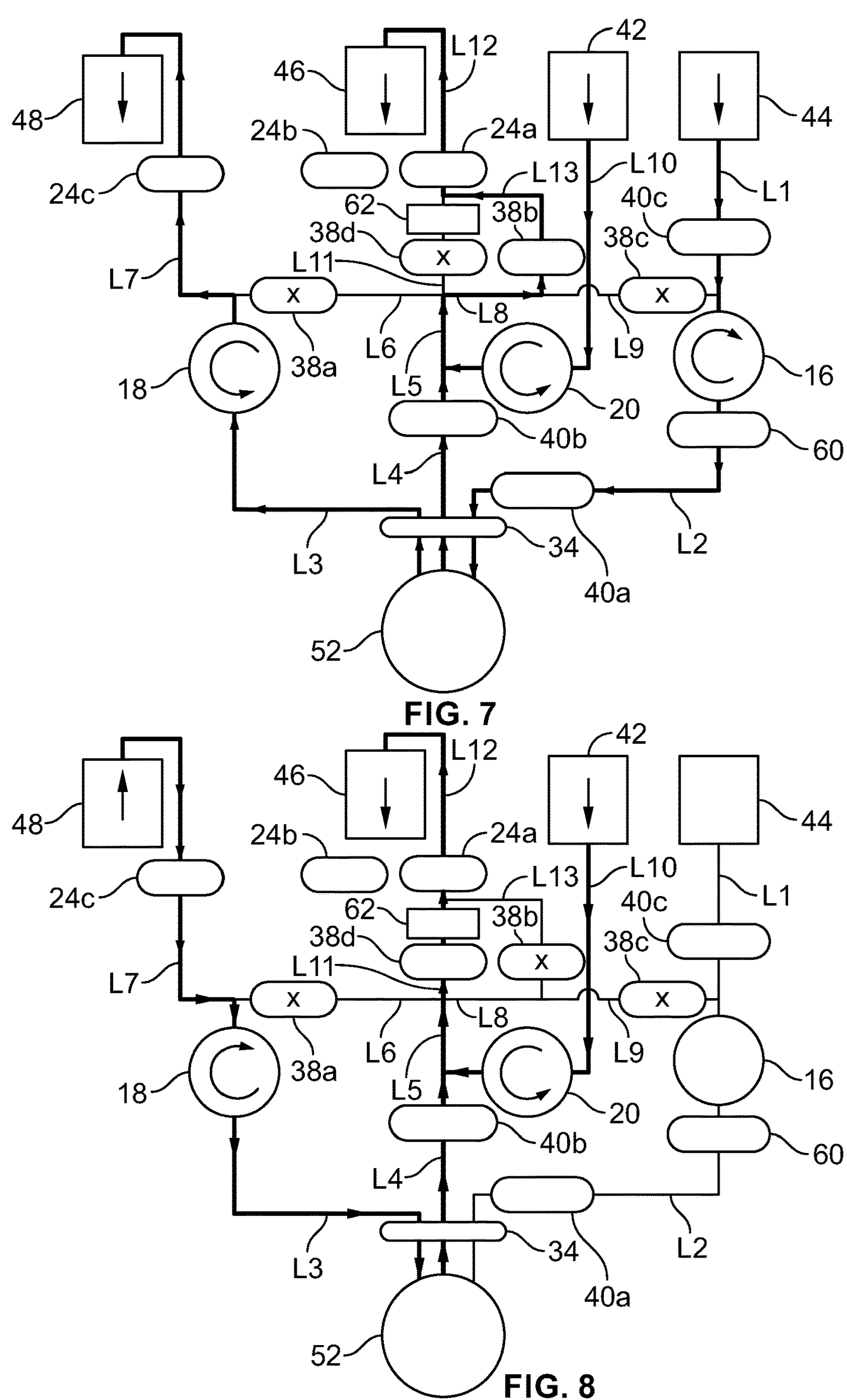
FIG. 7 is a schematic view of a variation of the "collection" stage of FIG. 6 in which the separated red blood cells are not leukoreduced before collection.
FIG. 8 is a schematic view of the blood processing system of FIG. 3 executing a "red blood cell recovery" stage of an exemplary blood processing procedure, with separated red blood cells being leukoreduced before collection.

As for the separated red blood cells, they exit the processing chamber 52 via the red blood cell outlet port and associated line L4. The additive pump 20 is operated by the controller to draw an additive solution (which is ADSOL® in one exemplary embodiment, but may be some other red blood cell additive) from the additive solution container 42 via line L10. The red blood cells flowing through line L4 are mixed with the additive solution flowing through line L10 at a junction of the two lines L4 and L10 to form a mixture that continues flowing into and through line L5. The mixture is ultimately directed into the red blood cell collection container 46, but may first be conveyed through a leukoreduction filter 62 (if provided), as shown in FIG. 6. Even if a leukoreduction filter 62 is provided, the valve system may be controlled to cause the mixture to bypass the leukoreduction filter 62 and enter the red blood cell collection container 46 without being leukoreduced, as shown in FIG. 7. It is also within the scope of the present disclosure for the mixture to be routed through the leukoreduction filter 62 at the beginning of the collection stage, with the valve system being reconfigured during the collection stage to cause the mixture to bypass the leukoreduction filter 62, such that only a portion of the collected red blood cells are leukoreduced.

In the configuration of FIG. 6 (in which the mixture is leukoreduced), valves 38*a*, 38*b*, and 38*c* are closed, while valve 38*d* is open, which directs the mixture from line L5 into line L11. The mixture flows through open valve 38*d* and the leukoreduction filter 62 and into line L12. The leukoreduced mixture then flows through open clamp 24*a* and into the red blood cell collection container 46.

In the configuration of FIG. 7 (in which the mixture is not leukoreduced), valves 38*a*, 38*c*, and 38*d* are closed, while valve 38*b* is open, which directs the mixture from line L5 into line L8 and then into line L13. The mixture flows through open valve 38*b* and into line L12, bypassing the leukoreduction filter 62. The non-leukoreduced mixture then flows through open clamp 24*a* and into the red blood cell collection container 46.

As described above, the mixture may be routed through the leukoreduction filter 62 at the beginning of the collection stage (as in FIG. 6), with the valve system being reconfigured during the collection stage to cause the mixture to bypass the leukoreduction filter 62 (as in FIG. 7), such that only a portion of the collected red blood cells are leukoreduced. In one embodiment, pressure sensor 40*b* monitors the pressure of the leukoreduction filter 62. If the pressure sensor 40*b* detects that the pressure of the leukoreduction filter 62 has risen above a predetermined pressure threshold (which may be indicative of filter blockage), the controller may reconfigure the valve system (from the configuration of FIG. 6 to the configuration of FIG. 7) to cause the mixture to bypass the leukoreduction filter 62. The system may then alert the operator that the red blood cell product was not leukoreduced.

Regardless of whether the collected red blood cells have been leukoreduced (or only partially leukoreduced), the collection stage continues until one unit of whole blood has been drawn into the fluid flow circuit 12 from the blood source. In the case of a whole blood container 44 being used as a blood source (as in the illustrated embodiment) the collection stage will end when the whole blood container 44 (which is initially provided with one unit of whole blood) is empty, with different approaches possibly being employed to determine when the whole blood container 44 is empty. For example, in one embodiment, pressure sensor 40*c* monitors the hydrostatic pressure of the whole blood container 44. An empty whole blood container 44 may be detected when the hydrostatic pressure measured by pressure sensor 40*c* is at or below a threshold value. Alternatively (or additionally), the weight of the whole blood container 44 may be monitored by a weight scale, with an empty whole blood container 44 being detected when the weight is at or below a threshold value. In the case of a living donor (or in the event that the whole blood container 44 is provided with more than one unit of blood), the volumetric flow rate of the whole blood pump 16 may be used to determine when one unit of whole blood has been drawn into the fluid flow circuit 12.

Once a total of one unit of whole blood has been drawn into the fluid flow circuit 12, the controller will transition the procedure to a "red blood cell recovery" stage, which is shown in FIG. 8. During the red blood cell recovery stage, air from the plasma collection container 48 (which was conveyed there during the blood prime stage) is used to recover the contents of the processing chamber 52 (which may be primarily red blood cells) to reduce product loss.

In the illustrated embodiment, the whole blood pump 16 is deactivated, while the plasma pump 18 is operated in a reverse direction (with respect to its direction of operation up to this stage of the procedure). This draws the air from the plasma collection container 48 and into line L7. Valve 38*a* is closed, while clamp 24*c* is open, which directs the air through line L7, into and through line L3, and into the processing chamber 52 via the plasma outlet port. On account of the air flowing through the plasma outlet port, it will enter the processing chamber 52 at the low-g side. As additional air is introduced into the processing chamber 52, it will move from the low-g wall towards the high-g wall, thus displacing any liquid content through the red blood cell outlet port at the high-g side and into line L4. During this stage, the centrifuge 22 may be operated at a slower rate (e.g., in the range of approximately 1,000-2,000 rpm) to decrease the risk of an air blockage (as during the blood prime stage).

The additive pump 20 continues its operation, drawing additive solution from the additive solution container 42 and through line L10, to be mixed with the contents of the processing chamber 52 flowing through line L4 at the junction of the two lines L4 and L10. The mixture continues flowing into and through line L5. If the valve system was arranged in the configuration of FIG. 6 at the end of the collection stage (so as to direct flow through the leukoreduction filter 62), valves 38*a*, 38*b*, and 38*c* may remain closed, with valve 38*d* being open to direct the mixture into line L11 for leukoreduction, as in FIG. 8. On the other hand, if the valve system was arranged in the configuration of FIG. 7 at the end of the collection stage (so as to bypass the leukoreduction filter 62), valves 38*a*, 38*c*, and 38*d* may remain closed, with valve 38*b* being open to direct the mixture through lines L8 and L13 to bypass the leukoreduction filter 62, as in FIG. 9. As described above with regard to the collection stage, it is possible for the controller to change the configurations of the valve system from the configuration shown in FIG. 8 to the configuration of FIG. 9 during the red blood cell recovery stage to stop leukoreduction of the mixture (e.g., if the pressure of the leukoreduction filter 62 becomes too great).

Regardless of whether the mixture is filtered, it flows into line L12, through open clamp 24*a*, and into the red blood cell collection container 46. The red blood cell recovery stage continues until all of the air is removed from the plasma collection container 48. In one exemplary embodiment, the weight of the plasma collection container 48 may be monitored by a weight scale, with an empty plasma collection container 48 being detected when the weight is at or below a threshold value. Other approaches may also be employed to determine when to end the red blood cell recovery stage, such as using the optical sensor 34 to detect plasma flowing through line L3.

Figures 9, 10:
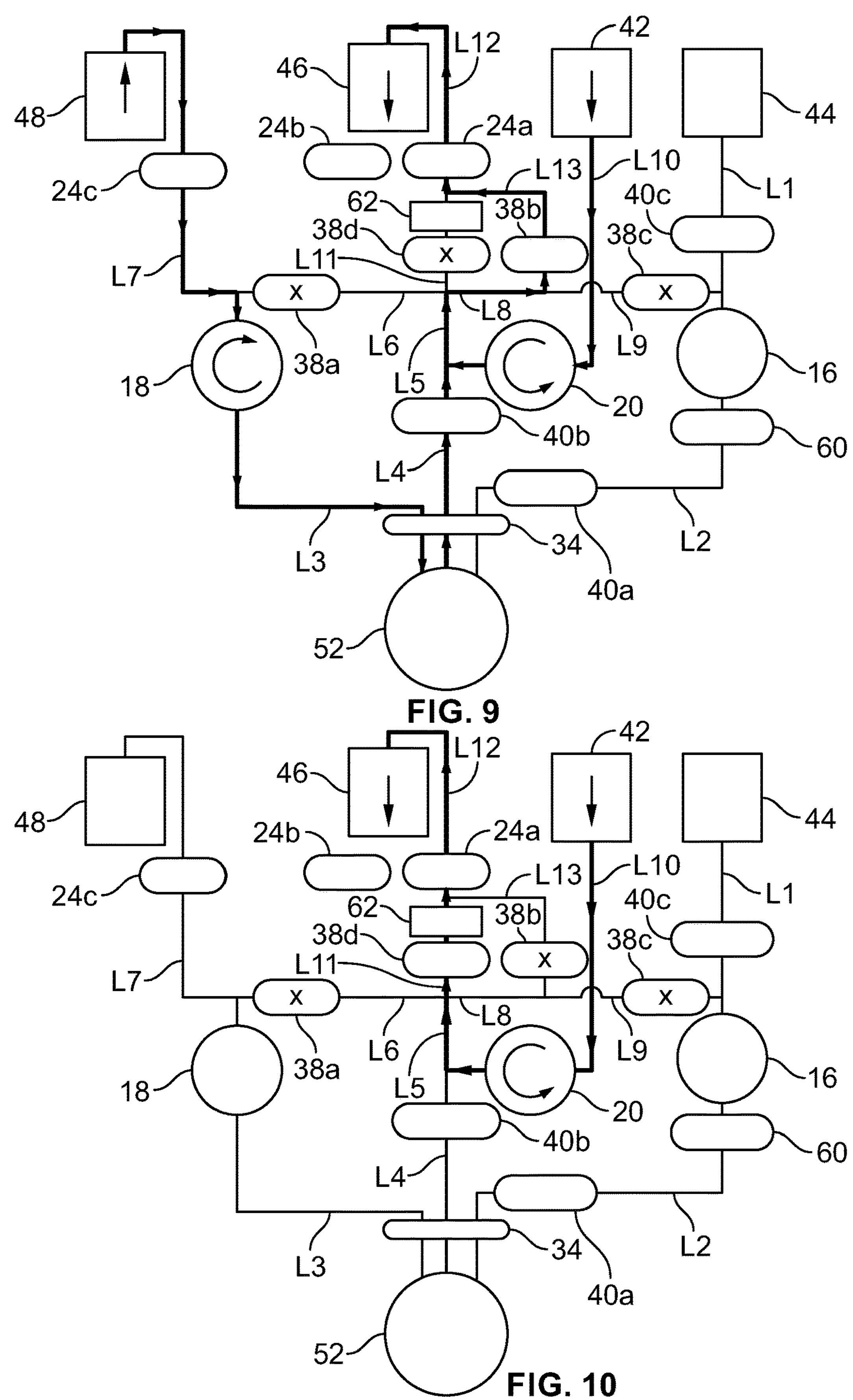
FIG. 9 is a schematic view of a variation of the "red blood cell recovery" stage of FIG. 8 in which the separated red blood cells are not leukoreduced before collection.
FIG. 10 is a schematic view of the blood processing system of FIG. 3 executing an "additive solution flush" stage of an exemplary blood processing procedure, with additive solution being directed through a leukoreduction filter before entering a red blood cell collection container.
Figures 11, 12:
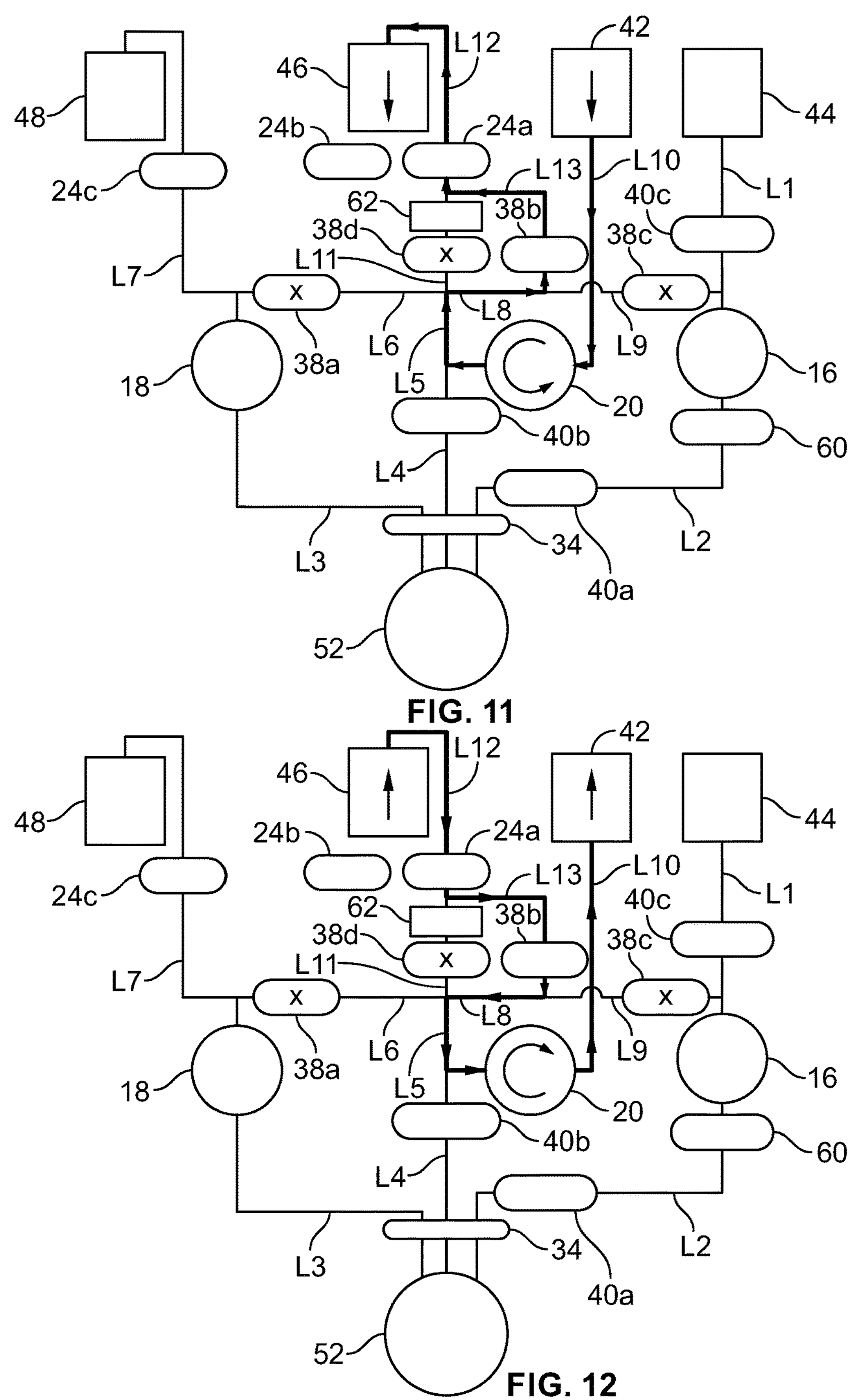
FIG. 11 is a schematic view of a variation of the "additive solution flush" stage of FIG. 10 in which the additive solution enters the red blood cell collection container without passing through the leukoreduction filter.
FIG. 12 is a schematic view of the blood processing system of FIG. 3 executing an "air evacuation" stage of an exemplary blood processing procedure.

Once the red blood cell recovery stage is complete, the procedure will transition to an "additive solution flush" stage. During the additive solution flush stage, additive solution from the additive solution container 42 is conveyed into the red blood cell collection container 46 until a target amount of additive solution is in the red blood cell collection container 46. The only change in transitioning from the red blood cell recovery stage to the additive solution flush stage involves deactivating the plasma pump to prevent plasma from being removed from the plasma collection container 48 (though it is also possible for the additive pump 20 to operate at a different rate). Thus, if the valve system was arranged to direct flow through the leukoreduction filter 62 at the end of the red blood cell recovery stage (as in FIG. 8), the additive solution flush stage will proceed as shown in FIG. 10. On the other hand, if the valve system was arranged to bypass the leukoreduction filter 62 at the end of the red blood cell recovery stage (as in FIG. 9), the additive solution flush stage will proceed as shown in FIG. 11. If the additive solution is pumped through the leukoreduction filter 62 during the additive solution flush stage (as in FIG. 10), the additive solution flowing through line L11 will flush residual red blood cells in the leukoreduction filter 62 into the red blood cell collection container 46 (in addition to achieving a proper additive solution volume for the red blood cell product).

The additive solution flush stage will continue until a target amount of additive solution has been added to the red blood cell collection container 46. In one exemplary embodiment, the weight of the additive solution container 42 may be monitored by a weight scale, with a particular change in weight corresponding to the target amount of additive solution having been conveyed to the red blood cell collection container 46. Alternatively (or additionally), the weight of the red blood cell collection container 46 may be monitored by a weight scale, with a particular change in weight corresponding to the target amount of additive solution having been conveyed to the red blood cell collection container 46.

When the additive solution flush stage is complete, the system will transition to an "air evacuation" stage, as shown in FIG. 12. During the air evacuation stage, the red blood cell collection container 46 is "burped" to remove all residual air for storage (just as air was removed from the plasma collection container 48 during the red blood cell recovery stage). This is done by reversing the direction of operation of the additive pump 20, closing valve 38*d* (if not already closed at the end of the additive solution flush stage), and opening valve 38*b* (if not already open at the end of the additive solution flush stage). The additive pump 20 draws air out of the red blood cell collection container 46, through line L12 and open clamp 24*a*, into line L13 and through open valve 38*b*. The air continues through line L8, line L5, and line L10, with the air ending up in the additive solution container 42. While FIG. 12 shows the air being evacuated from the red blood cell collection container 46 to the additive solution container 42, it is within the scope of the present disclosure for all or a portion of the air to be directed to a different location of the fluid flow circuit 12 (e.g., into the processing chamber 52 and/or into the whole blood container 44, if provided).

The air evacuation stage will continue until all of the air is removed from the red blood cell collection container 46, which may be determined (for example) by detecting a change in the weight of the red blood cell collection container 46 (e.g., using a weight scale).

Figures 13, 14:
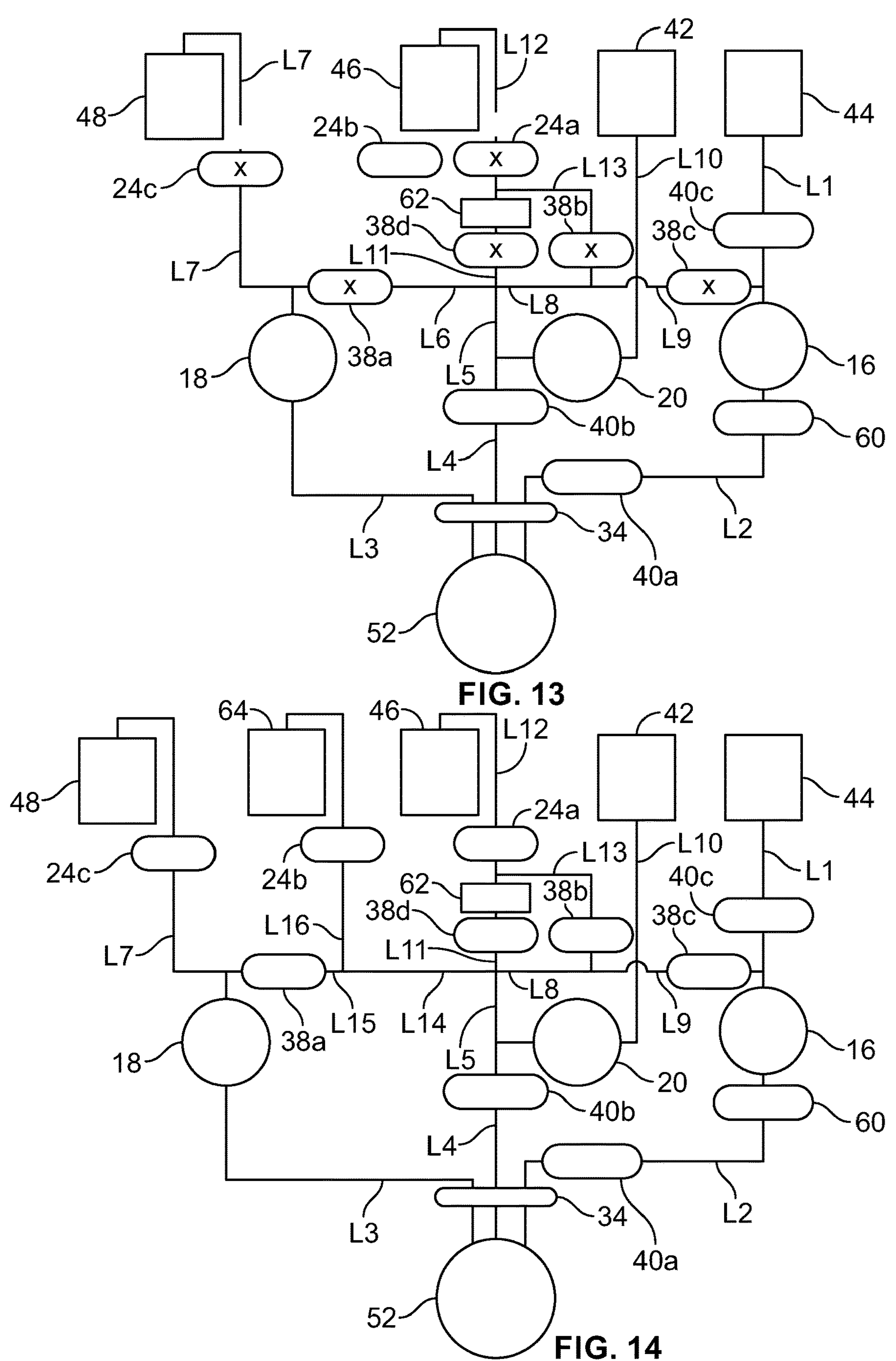
FIG. 13 is a schematic view of the blood processing system of FIG. 3 executing a "sealing" stage of an exemplary blood processing procedure.
FIG. 14 is a schematic view of another embodiment of a fluid flow circuit mounted to the processing device of FIG. 1 to complete a blood processing system according to an aspect of the present disclosure.

Upon completion of the air evacuation stage, any of a number of post-processing stages may be executed. For example, FIG. 13 shows a "sealing" stage in which all of the clamps and valves are closed and all of the pumps are deactivated. The line L12 connected to the red blood cell collection container 46 and the line L7 connected to the plasma collection container 48 are sealed and optionally severed for storage of the plasma and red blood cell products. If lines L7 and L12 are severed, the plasma collection container 48 and the red blood cell collection container 46 may be stored, while the remainder of the fluid flow circuit 12 is disposed of. Lines L7 and L12 may be sealed (and optionally severed) according to any suitable approach, which may include being sealed by RF sealers incorporated or associated with clamps 24*a* and 24*c*, for example. In another embodiment, the fluid flow circuit 12 may be removed from the processing device 10, with lines L7 and L12 being sealed (and optionally severed) using a dedicated sealing device.

Red Blood Cell, Plasma, and Buffy Coat Product Collection

As described above, providing the processing chamber 52 with a plasma outlet port that is spaced from and positioned downstream of the blood inlet port allows the interface between separated plasma and red blood cells in the processing chamber 52 to develop into a platelet- and mononuclear cell-containing layer referred to as a buffy coat. While the buffy coat is not collected in the procedure shown in FIGS. 4-13, according to a variation of that procedure, the processing device 10 may be used in combination with a suitably configured fluid flow circuit to process a unit of whole blood into separate red blood cell, plasma, and buffy coat products.

An exemplary fluid flow circuit is shown in FIG. 14, which also shows selected components of the processing device 10. Due to the similarity between the fluid flow circuits of FIGS. 3 and 14, the components of the fluid flow circuit of FIG. 14 corresponding to above-described components of the fluid flow circuit of FIG. 3 will be identified using the same reference numbers, while new or differently configured components will be identified using new reference numbers. In short, the principal difference between the fluid flow circuit of FIG. 3 and the fluid flow circuit of FIG. 14 is that line L6 of the fluid flow circuit of FIG. 3 is replaced in the fluid flow circuit of FIG. 14 with a pair of lines L14 and L15 that meet at a junction, with a third line L16 leading from the junction to a buffy coat collection container 64. Whereas clamp 24*b* of the processing device 10 is not used with the fluid flow circuit of FIG. 3, it will be seen that it is associated with line L16 of the fluid flow circuit of FIG. 14 and used during an exemplary procedure that will be described in greater detail below.

FIGS. 15-25 show different stages of an exemplary procedure for collecting red blood cell, plasma, and buffy coat products. Many of the stages illustrated in FIGS. 15-25 are similar to above-described stages of the procedure shown in FIGS. 4-13. Such stages will be described below with reference to the corresponding stage of the procedure of FIGS. 4-13, and it should be understood that such stages proceed according to the above description of the corresponding stage of the procedure of FIGS. 4-13, unless stated to the contrary.

Figures 15, 16:
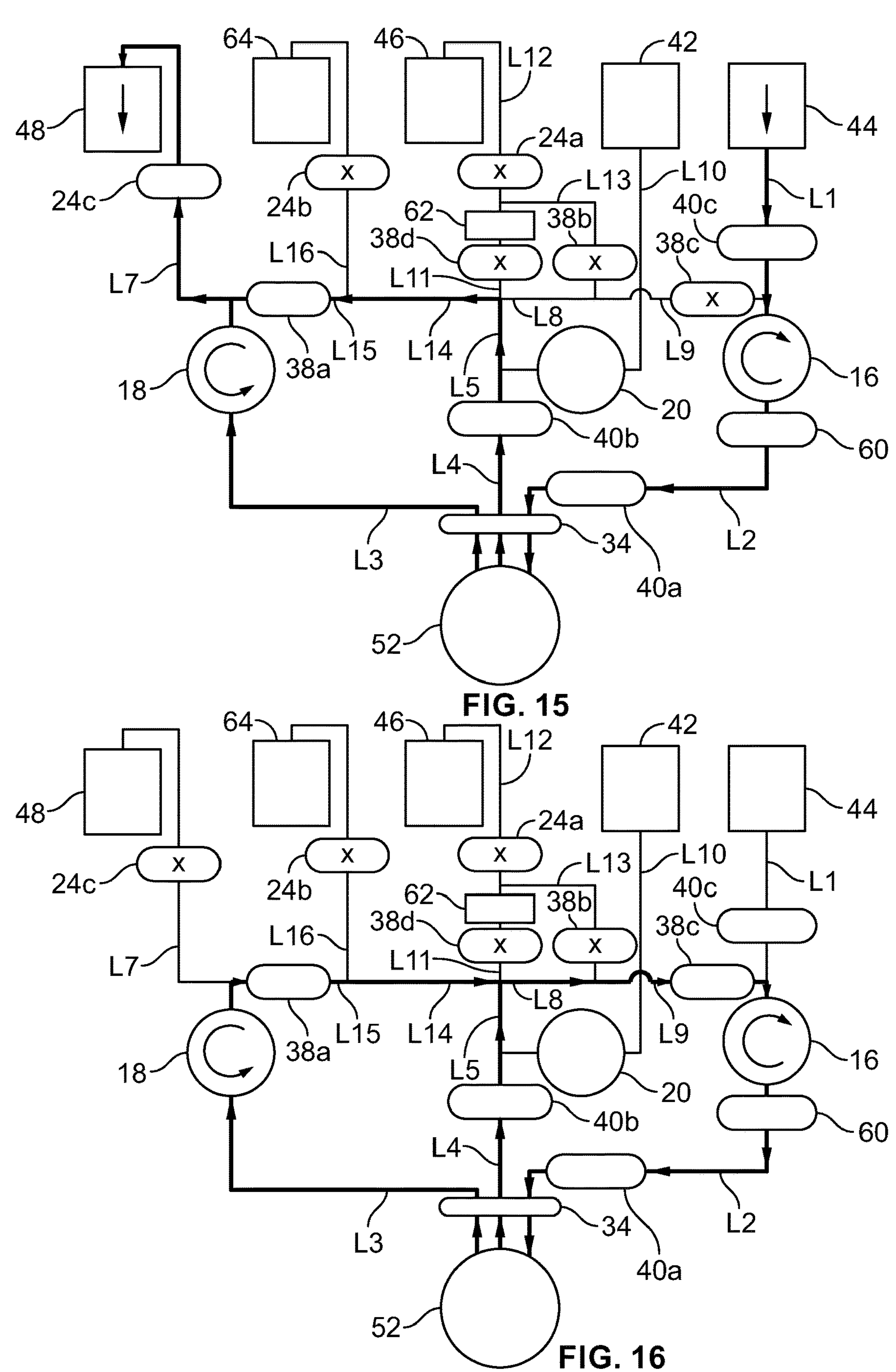
FIG. 15 is a schematic view of the blood processing system of FIG. 14 executing a "blood prime" stage of an exemplary blood processing procedure.
FIG. 16 is a schematic view of the blood processing system of FIG. 14 executing an "establish separation" stage of an exemplary blood processing procedure.

The illustrated procedure begins with a "blood prime" stage (FIG. 15) that corresponds to the blood prime stage shown in FIG. 4 and described above, with selected components of the fluid flow circuit being primed using blood from a blood source. In accordance with the above description of the procedure of FIGS. 4-13, the blood source is shown in FIG. 15 as the whole blood container 44, but may alternatively be a living donor.

During the blood prime stage, whole blood is drawn into the fluid flow circuit from the blood source (the whole blood container 44 in the embodiment of FIG. 15) via line L1 by operation of the whole blood pump 16. Valve 38*c* is closed, which directs the blood through pressure sensor 40*c* and into line L2. The blood passes through air trap 60, pressure sensor 40*a*, and optical sensor 34 before flowing into the processing chamber 52, which is positioned within the centrifuge 22 of the processing device 10. In accordance with the above description of the blood prime stage of FIG. 4, the centrifuge 22 may be stationary during the blood prime stage of FIG. 15 or may be spun at a low rate (e.g., on the order of approximately 1,000-2,000 rpm).

The blood entering the processing chamber 52 will move towards the high-g (radially outer) wall of the processing chamber 52, displacing air towards the low-g wall. Most of the air will exit the processing chamber 52 via the plasma outlet port and associated line L3, although some air may also exit the processing chamber 52 via the red blood cell outlet port and associated line L4.

Valves 38*b* and 38*d* are closed, while the plasma pump 18 is active and the additive pump 20 is inactive. This directs the air exiting the processing chamber 52 via the red blood cell outlet port through associated line L4 and pressure sensor 40*b*, into line L5 and then into line L14. Clamp 24*b* is closed, while valve 38*a* is open, such that the air flowing through line L14 will flow into line L15 and then meet up with the air flowing through line L3 (i.e., the air that exits the processing chamber 52 via the plasma outlet port). The combined air will flow through line L7 and open clamp 24*c*, into the plasma collection container 48. The blood prime stage continues until a non-air fluid is detected in both lines L3 and L4.

The next stage (shown in FIG. 16) is an "establish separation" stage that corresponds to the establish separation stage shown in FIG. 5 and described above. In accordance with the above description of the establish separation stage of FIG. 5, the rotational speed of the centrifuge 22 is increased to a rate that is sufficient to separate blood into packed red blood cells and platelet-poor plasma, with the buffy coat therebetween (e.g., in the range of approximately 4,500 to 5,500 rpm), while the whole blood pump 16 continues operating (but without drawing additional blood into the fluid flow circuit from the blood source).

Separated plasma will exit the processing chamber 52 via the plasma outlet port and associated line L3. Clamps 24*b* and 24*c* are closed during this stage, while valve 38*a* remains open, which directs the plasma from line L3 into line L15 and then into line L14. Separated red blood cells exit the processing chamber 52 via the red blood cell outlet port and associated line L4, while the buffy coat remains in the processing chamber 52. As explained above with regard to the procedure of FIGS. 4-13, there is no pump shown in association with line L4 (such that the red blood cells exit the processing chamber 52 at a rate that is equal to the difference between the rate of the whole blood pump 16 and the rate of the plasma pump 18), though it is within the scope of the present disclosure for there to be a pump associated with the red blood cell outlet line instead of the plasma outlet line or a first pump associated with the plasma outlet line and a second pump associated with the red blood cell outlet line.

The additive pump 20 is inactive during this stage, thereby directing the red blood cells from line L4 into line L5. The plasma flowing through line L14 is mixed with the red blood cells flowing through line L5 at the junction of the two lines L5 and L14 to form recombined whole blood. Valve 38*d* is closed, which directs the recombined whole blood into line L8. Valve 38*b* is also closed, which directs the recombined whole blood from line L8 into line L9 and through open valve 38*c*. The whole blood pump 16 draws the recombined whole blood into line L2 from line L9 (rather than drawing additional blood into the fluid flow circuit 12 from the blood source), with the recombined blood passing through air trap 60, pressure sensor 40*a*, and optical sensor 34 before flowing back into the processing chamber 52, where it is again separated into plasma and red blood cells, with the buffy coat therebetween.

The establish separation stage continues until steady state separation has been achieved, preferably with the interface between the separated plasma and the separated red blood cells and buffy coat within the processing chamber 52 at a target location. An exemplary approach for moving the interface to a target location within the processing chamber 52 is described above in greater detail with regard to the establish separation stage of FIG. 5.

Once steady state separation has been established, the controller ends the establish separation stage and advances the procedure to a "collection" stage (FIG. 17) that corresponds to the collection stage shown in FIG. 6 and described above. At the beginning of the collection stage, the centrifuge 22, the whole blood pump 16, and the plasma pump 18 all continue operating at the same rates at which they were operating at the end of the establish separation stage. The valve system of the processing device 10, however, is adjusted to direct the separated plasma and red blood cells to their respective collection containers (rather than recombining them and recirculating them through the centrifuge 22), while causing additional blood to be drawn into the fluid flow circuit from the blood source until a total of one unit of whole blood has been drawn into the fluid flow circuit. As in the establish separation stage, the buffy coat remains in the processing chamber 52 during the collection stage.

More particularly, during the collection stage, valve 38*c* is closed, which causes the whole blood pump 16 to draw additional blood into line L1 from the blood source. The whole blood pump 16 draws the blood from the blood source into line L2 from line L1, with the blood passing through air trap 60, pressure sensor 40*a*, and optical sensor 34 before flowing into the processing chamber 52, where it is separated into plasma, red blood cells, and buffy coat.

The separated plasma exits the processing chamber 52 via the plasma outlet port and associated line L3. Valve 38*a* is closed, which directs the plasma from line L3 into line L7, through open clamp 24*c*, and into the plasma collection container 48.

Figures 17, 18:
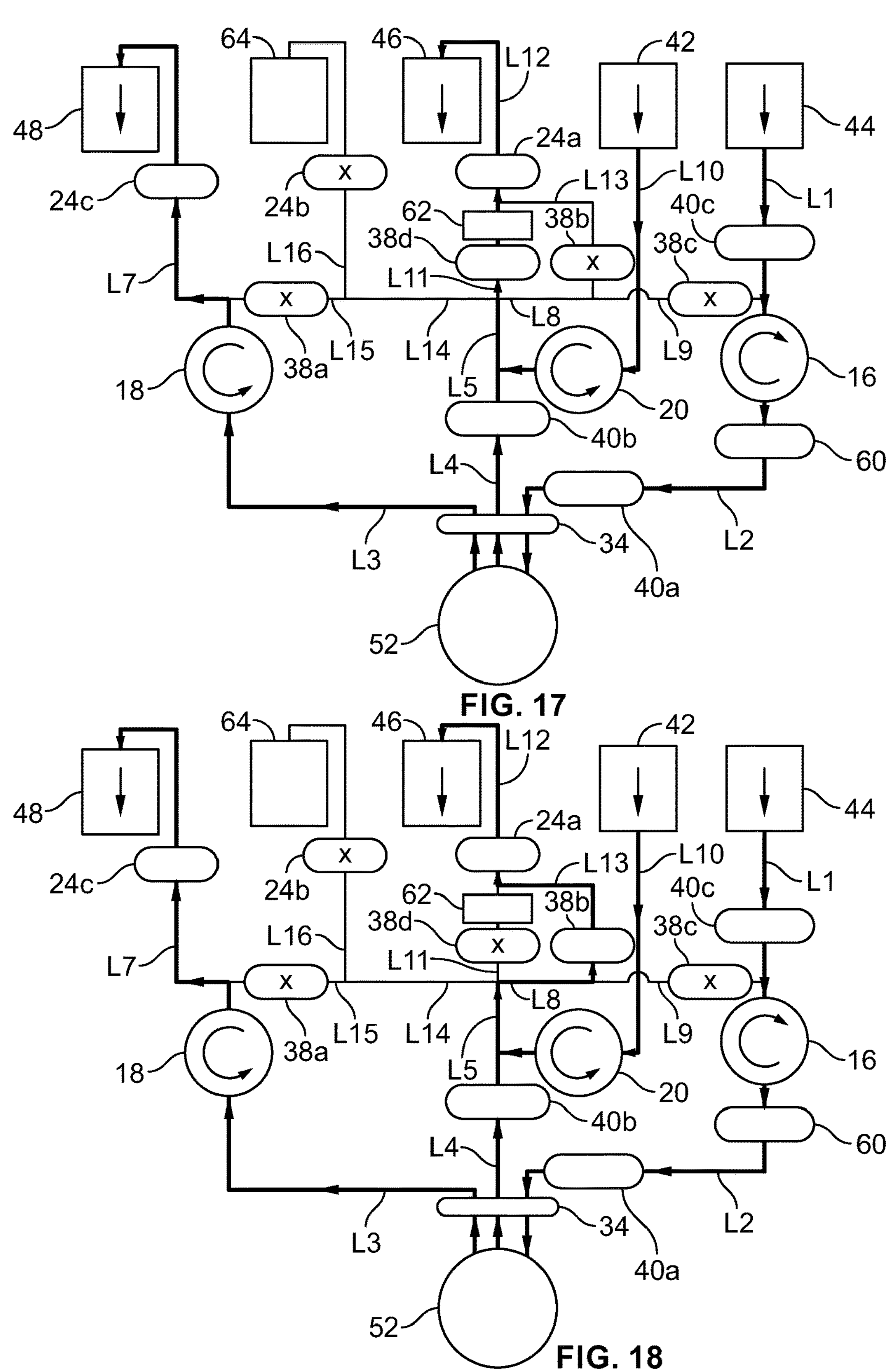
FIG. 17 is a schematic view of the blood processing system of FIG. 14 executing a "collection" stage of an exemplary blood processing procedure, with separated red blood cells being leukoreduced before collection.
FIG. 18 is a schematic view of a variation of the "collection" stage of FIG. 17 in which the separated red blood cells are not leukoreduced before collection.

The separated red blood cells exit the processing chamber 52 via the red blood cell outlet port and associated line L4. The additive pump 20 is operated by the controller to draw an additive solution (which may be ADSOL® or some other red blood cell additive) from the additive solution container 42 via line L10. The red blood cells flowing through line L4 are mixed with the additive solution flowing through line L10 at a junction of the two lines L4 and L10 to form a mixture that continues flowing into and through line L5. The mixture is ultimately directed into the red blood cell collection container 46, but may first be conveyed through a leukoreduction filter 62 (if provided), as shown in FIG. 17 (in accordance with the above description of the collection stage of FIG. 6). Even if a leukoreduction filter 62 is provided, the valve system may be controlled to cause the mixture to bypass the leukoreduction filter 62 and enter the red blood cell collection container 46 without being leukoreduced, as shown in FIG. 18 (in accordance with the above description of the collection stage of FIG. 7). It is also within the scope of the present disclosure for the mixture to be routed through the leukoreduction filter 62 at the beginning of the collection stage, with the valve system being reconfigured during the collection stage to cause the mixture to bypass the leukoreduction filter 62, such that only a portion of the collected red blood cells are leukoreduced.

The collection stage continues until one unit of whole blood has been drawn into the fluid flow circuit from the blood source. In the case of a whole blood container 44 being used as a blood source (as in the illustrated embodiment) the collection stage will end when the whole blood container 44 (which is initially provided with one unit of whole blood) is empty. In the case of a living donor (or in the event that the whole blood container 44 is provided with more than one unit of blood), the volumetric flow rate of the whole blood pump 16 may be used to determine when one unit of whole blood has been drawn into the fluid flow circuit.

Figures 19, 20:
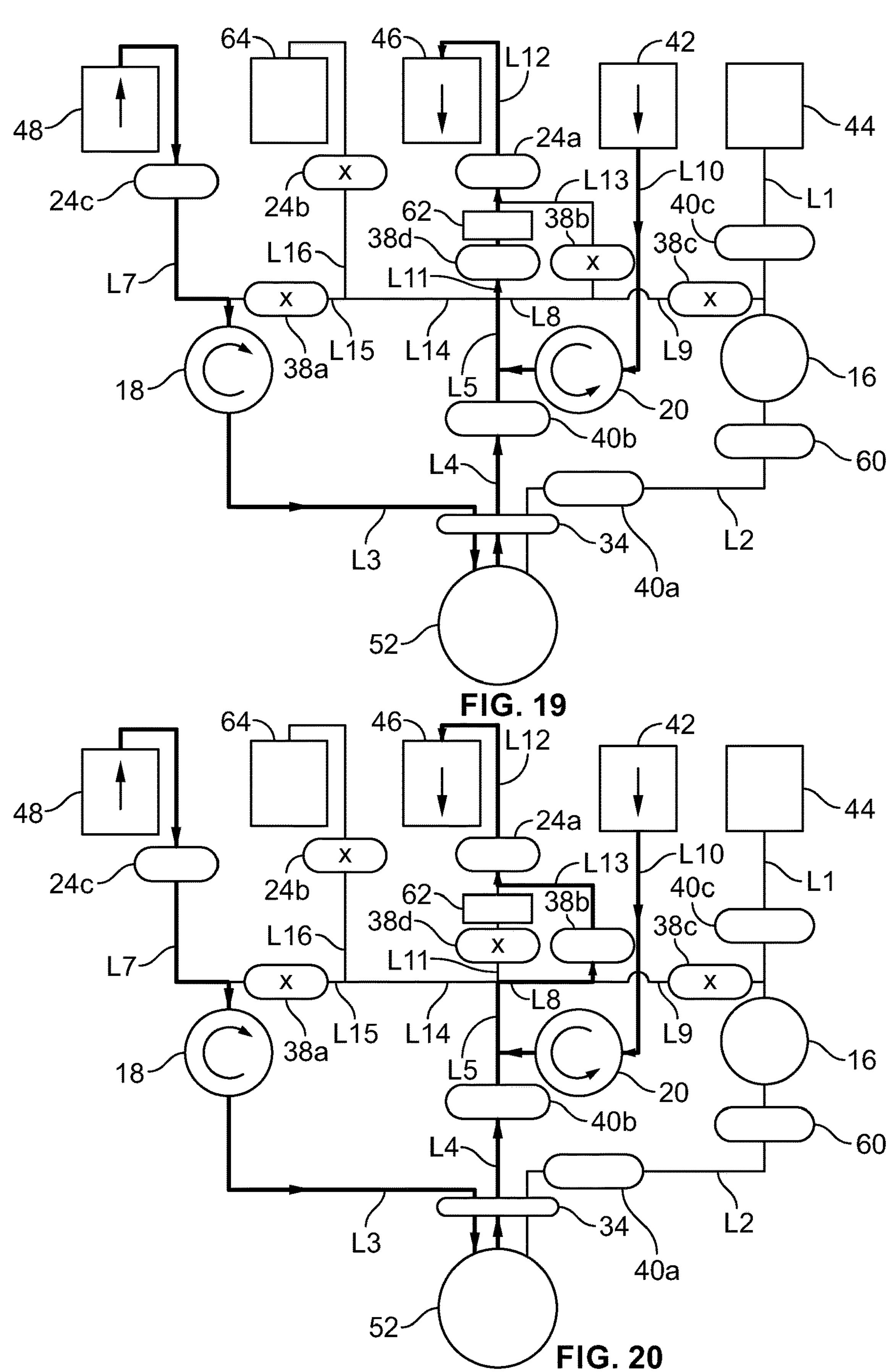
FIG. 19 is a schematic view of the blood processing system of FIG. 14 executing a "red blood cell recovery" stage of an exemplary blood processing procedure, with recovered red blood cells being leukoreduced before collection.
FIG. 20 is a schematic view of a variation of the "red blood cell recovery" stage of FIG. 19 in which the recovered red blood cells are not leukoreduced before collection.

Once a total of one unit of whole blood has been drawn into the fluid flow circuit, the controller will transition the procedure to a "red blood cell recovery" stage, which is shown in FIG. 19. During the red blood cell recovery stage, air from the plasma collection container 48 (which was conveyed there during the blood prime stage) is used to recover separated red blood cells remaining in the processing chamber 52 without removing the buffy coat from the processing chamber 52.

In the illustrated embodiment, the whole blood pump 16 is deactivated, while the plasma pump 18 is operated in a reverse direction (with respect to its direction of operation up to this stage of the procedure). This draws the air from the plasma collection container 48 and into line L7. Valve 38*a* is closed, while clamp 24*c* is open, which directs the air through line L7, into and through line L3, and into the processing chamber 52 via the plasma outlet port. On account of the air flowing through the plasma outlet port, it will enter the processing chamber 52 at the low-g side. As additional air is introduced into the processing chamber 52, it will move from the low-g wall towards the high-g wall, thus displacing the separated red blood cells in the processing chamber 52 through the red blood cell outlet port at the high-g side and into line L4. During this stage, the centrifuge 22 may be operated at a slower rate (e.g., in the range of approximately 1,000-2,000 rpm) to decrease the risk of an air blockage.

The additive pump 20 continues its operation, drawing additive solution from the additive solution container 42 and through line L10, to be mixed with the red blood cells flowing through line L4 at the junction of the two lines L4 and L10. The mixture continues flowing into and through line L5. If the valve system was arranged in the configuration of FIG. 17 at the end of the collection stage (so as to direct flow through the leukoreduction filter 62), valves 38*a*, 38*b*, and 38*c* may remain closed, with valve 38*d* being open to direct the mixture into line L11 for leukoreduction, as in FIG. 19. On the other hand, if the valve system was arranged in the configuration of FIG. 18 at the end of the collection stage (so as to bypass the leukoreduction filter 62), valves 38*a*, 38*c*, and 38*d* may remain closed, with valve 38*b* being open to direct the mixture through lines L8 and L13 to bypass the leukoreduction filter 62, as in FIG. 20. As described above with regard to the collection stage, it is possible for the controller to change the configurations of the valve system from the configuration shown in FIG. 19 to the configuration of FIG. 20 during the red blood cell recovery stage to stop leukoreduction of the mixture (e.g., if the pressure of the leukoreduction filter 62 becomes too great).

Regardless of whether the mixture is filtered, it flows into line L12, through open clamp 24*a*, and into the red blood cell collection container 46. The red blood cell recovery stage continues until the red blood cells have been removed from the processing chamber 52. This may be determined in any of a number of ways without departing from the scope of the present disclosure. In one embodiment, the red blood cell recovery stage continues until a predetermined volume of fluid (corresponding to the volume of red blood cells remaining in the processing chamber 52) has been conveyed out of the processing chamber 52. This volume may be calculated for example, by determining the volume of red blood cells present in the one unit of whole blood (which may be determined based on the hematocrit of the blood) and then subtracting the volume of red blood cells that have already been conveyed into the red blood cell collection container 46 (which may be determined based on the weights of the red blood cell container and the additive solution container 42 at the end of the collection stage). In another embodiment, the red blood cell recovery stage may continue until the optical sensor 34 detects a non-red blood cell fluid (e.g., the buffy coat) flowing through line L4.

Figures 21, 22:
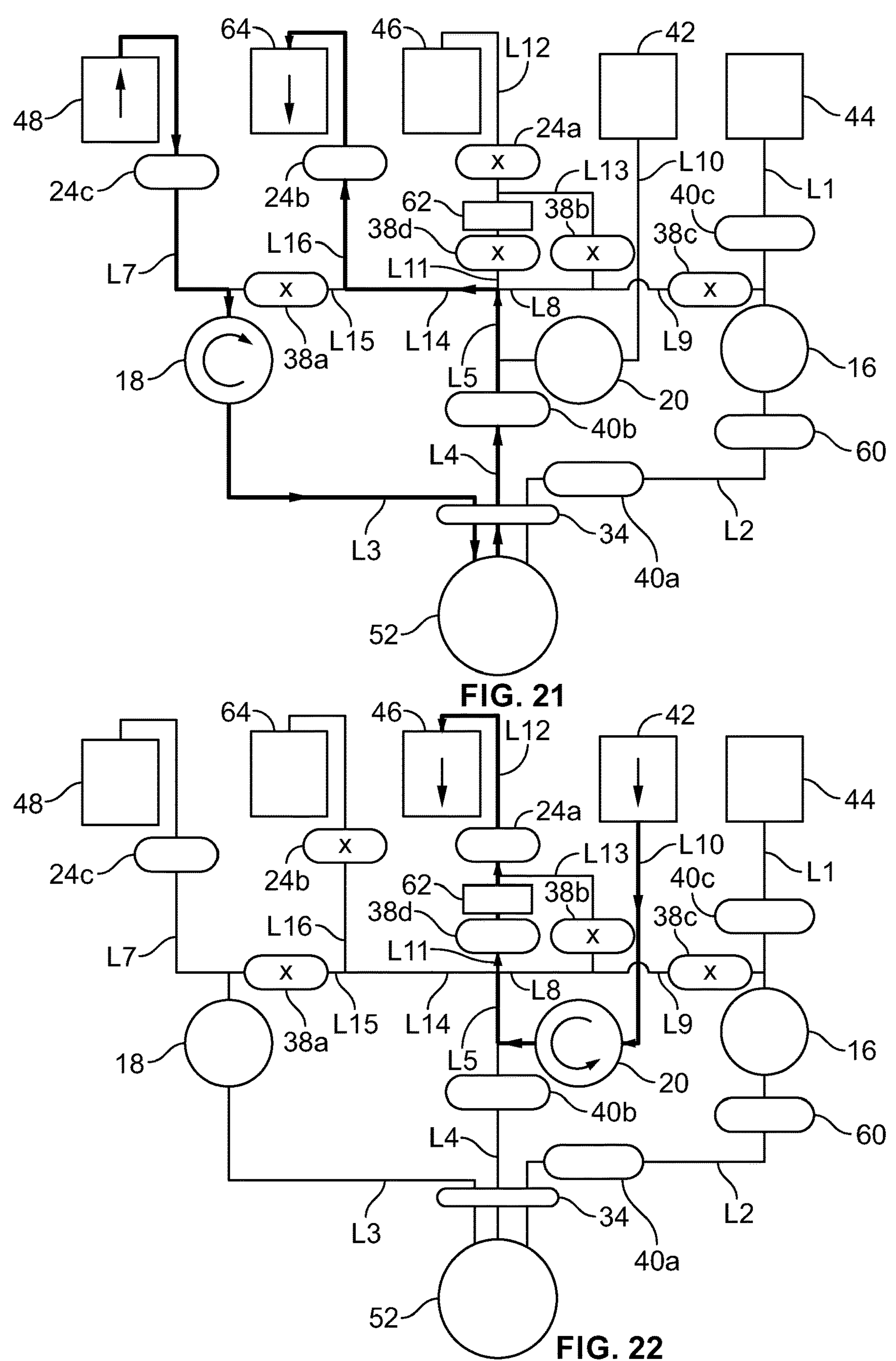
FIG. 21 is a schematic view of the blood processing system of FIG. 14 executing a "buffy coat harvest" stage of an exemplary blood processing procedure.
FIG. 22 is a schematic view of the blood processing system of FIG. 14 executing an "additive solution flush" stage of an exemplary blood processing procedure, with additive solution being directed through a leukoreduction filter before entering a red blood cell collection container.

Some air will remain in the plasma collection container 48 at the end of the red blood cell recovery stages of FIGS. 19 and 20. At least a portion of the air remaining in the plasma collection container 48 is used in a "buffy coat harvest" stage (which is shown in FIG. 21) to convey the buffy coat in the processing chamber 52 into the buffy coat collection container 64 as a buffy coat product. Due to air being conveyed through the processing chamber 52 during the buffy coat harvest stage, the centrifuge 22 may continue operating at a relatively low rate (e.g., in the range of approximately 1,000-2,000 rpm, as during the red blood cell recovery stage) to decrease the risk of an air blockage.

To transition from the red blood cell recovery stage to the buffy coat harvest stage, clamp 24*b* is opened, while clamp 24*a* is closed. One of valves 38*b* and 38*d* will be open at the end of the red blood cell recovery stage, while the other is closed (depending on whether the mixture of red blood cells and additive solution is routed through or around the leukoreduction filter 62. Whichever of the two valves 38*b* and 38*d* is open at the end of the red blood cell recovery stage is closed upon transitioning to the buffy coat harvest stage, such that both valves 38*b* and 38*d* are closed during the buffy coat harvest stage. The additive pump 20 is also stopped upon transitioning to the buffy coat harvest stage.

With the various clamps, valves, and pumps being configured as shown in FIG. 21, the plasma pump 18 will continue drawing air from the plasma collection container 48 into the processing chamber 52 via lines L7 and L3. As in the red blood cell recovery stage, the air will enter the processing chamber 52 at the low-g side and move from the low-g wall toward the high-g wall as additional air is conveyed into the processing chamber 52. This displaces the buffy coat remaining in the processing chamber 52 through the red blood cell outlet port at the high-g side and into line L4. The buffy coat is directed from line L4 into line L5 and then into line L14. From line L14, the buffy coat is directed into line L16, through open clamp 24*b*, and into the buffy coat collection container 64 as a buffy coat product.

The buffy coat harvest stage continues until the buffy coat has been removed from the processing chamber 52. This may be determined in any of a number of ways without departing from the scope of the present disclosure. In one embodiment, the buffy coat harvest stage continues until a predetermined volume of fluid (corresponding to the volume of the buffy coat or interface in the processing chamber 52) has been conveyed out of the processing chamber 52. This volume may be calculated for example, by subtracting the volumes of collected plasma and collected red blood cells at the end of the red blood cell recovery stage from the volume of blood that has been processed. In another embodiment, the buffy coat harvest stage may continue until the optical sensor 34 detects a non-buffy coat fluid (e.g., air) flowing through line L4.

Figures 23, 24:
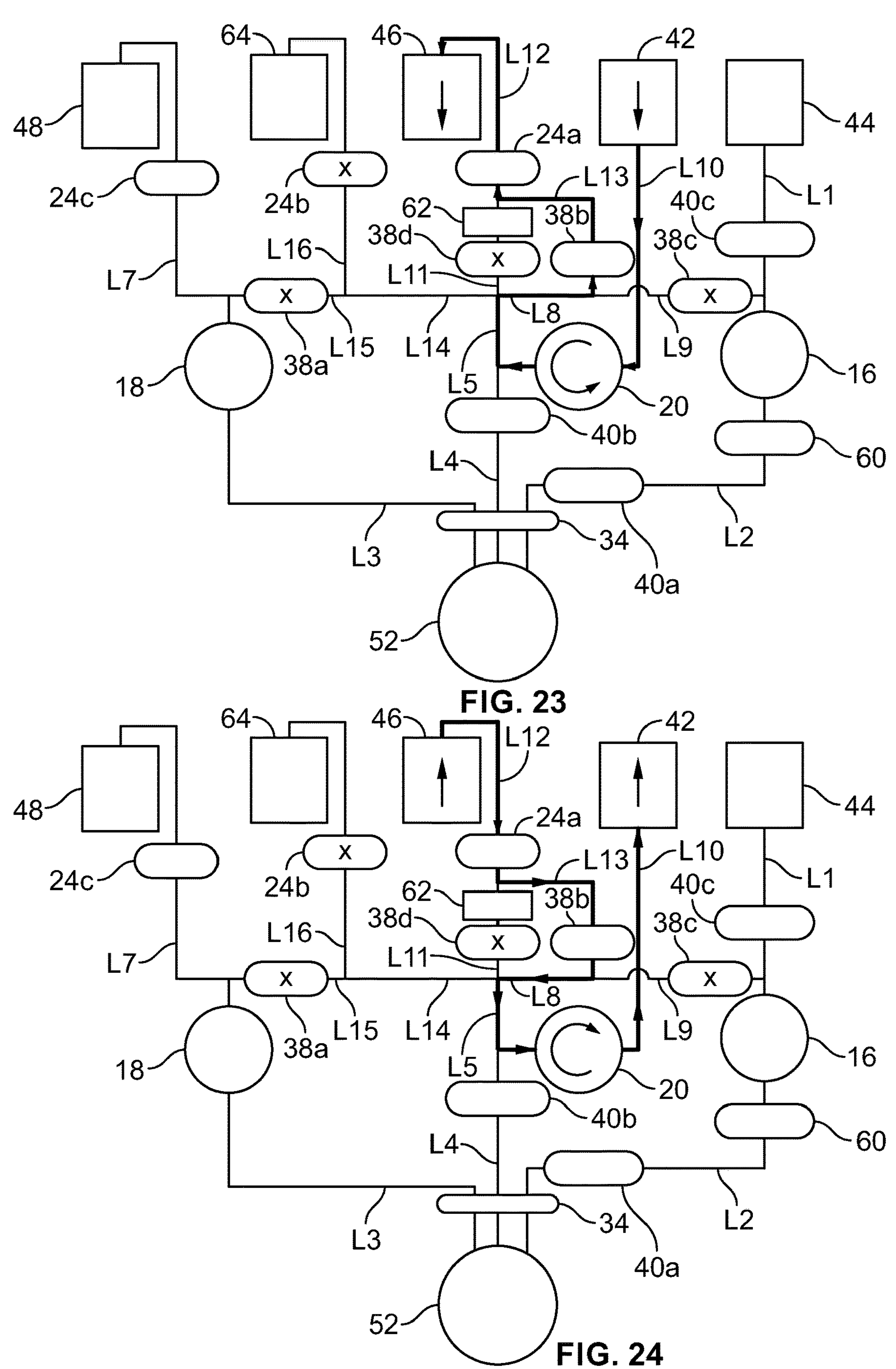
FIG. 23 is a schematic view of a variation of the "additive solution flush" stage of FIG. 22 in which the additive solution enters the red blood cell collection container without passing through the leukoreduction filter.
FIG. 24 is a schematic view of the blood processing system of FIG. 14 executing an "air evacuation" stage of an exemplary blood processing procedure.

Once the buffy coat harvest stage is complete, the procedure will transition to an "additive solution flush" stage (FIGS. 22 and 23). During the additive solution flush stage (as described above with regard to the additive solution flush stages of FIGS. 10 and 11), additive solution from the additive solution container 42 is conveyed into the red blood cell collection container 46 until a target amount of additive solution is in the red blood cell collection container 46.

To transition from the buffy coat harvest stage to the additive solution flush stage, clamp 24*b* is closed, clamp 24*a* is opened, the plasma pump 18 is deactivated, and the additive pump 20 is reactivated. Additionally, one of valves 38*b* and 38*d* is opened, which determines whether the additive solution will be conveyed through the leukoreduction filter 62 (FIG. 22) or routed around the leukoreduction filter 62 (FIG. 23) and which may depend on which of the two valves 38*b* and 38*d* was open at the end of the red blood cell recovery stage. Typically, if valve 38*d* was open at the end of the red blood cell recovery stage (as in FIG. 19), it will be opened at the beginning of the additive solution flush stage (as in FIG. 22) to allow for red blood cells remaining in the leukoreduction filter 62 to be recovered by additive solution being conveyed through the leukoreduction filter 62. Similarly, if valve 38*b* was open at the end of the red blood cell recovery stage (as in FIG. 20), it will be opened at the beginning of the additive solution flush stage (as in FIG. 23) to direct additive solution around the leukoreduction filter 62. However, it is also within the scope of the present disclosure for valve 38*b* to be closed and valve 38*d* to be open at the end of the red blood cell recovery stage (as in FIG. 19), with valve 38*b* being open and valve 38*d* being closed at the beginning of the additive solution flush stage (as in FIG. 23), if the controller determines that it is advisable to begin bypassing the leukoreduction filter 62. Additionally, it is within the scope of the present disclosure for the valve system to be arranged as in FIG. 22 at the beginning of the additive solution flush stage (to direct additive solution through the leukoreduction filter 62) and to transition into the configuration of FIG. 23 before the end of the additive solution flush stage (to cause the additive solution to bypass the leukoreduction filter 62).

The additive solution flush stage will continue until a target amount of additive solution has been added to the red blood cell collection container 46. When the additive solution flush stage is complete, the system will transition to an "air evacuation" stage, as shown in FIG. 24. During the air evacuation stage, the red blood cell collection container 46 is "burped" to remove all residual air for storage (just as air was removed from the plasma collection container 48 during the red blood cell recovery and buffy coat harvest stages). This is done by reversing the direction of operation of the additive pump 20, closing valve 38*d* (if not already closed at the end of the additive solution flush stage), and opening valve 38*b* (if not already open at the end of the additive solution flush stage). The additive pump 20 draws air out of the red blood cell collection container 46 and into the additive solution container 42, in accordance with the above description of the air evacuation stage of FIG. 12. While FIG. 24 shows the air being evacuated from the red blood cell collection container 46 to the additive solution container 42, it is within the scope of the present disclosure for all or a portion of the air to be directed to a different location of the fluid flow circuit.

Figures 25, 26:
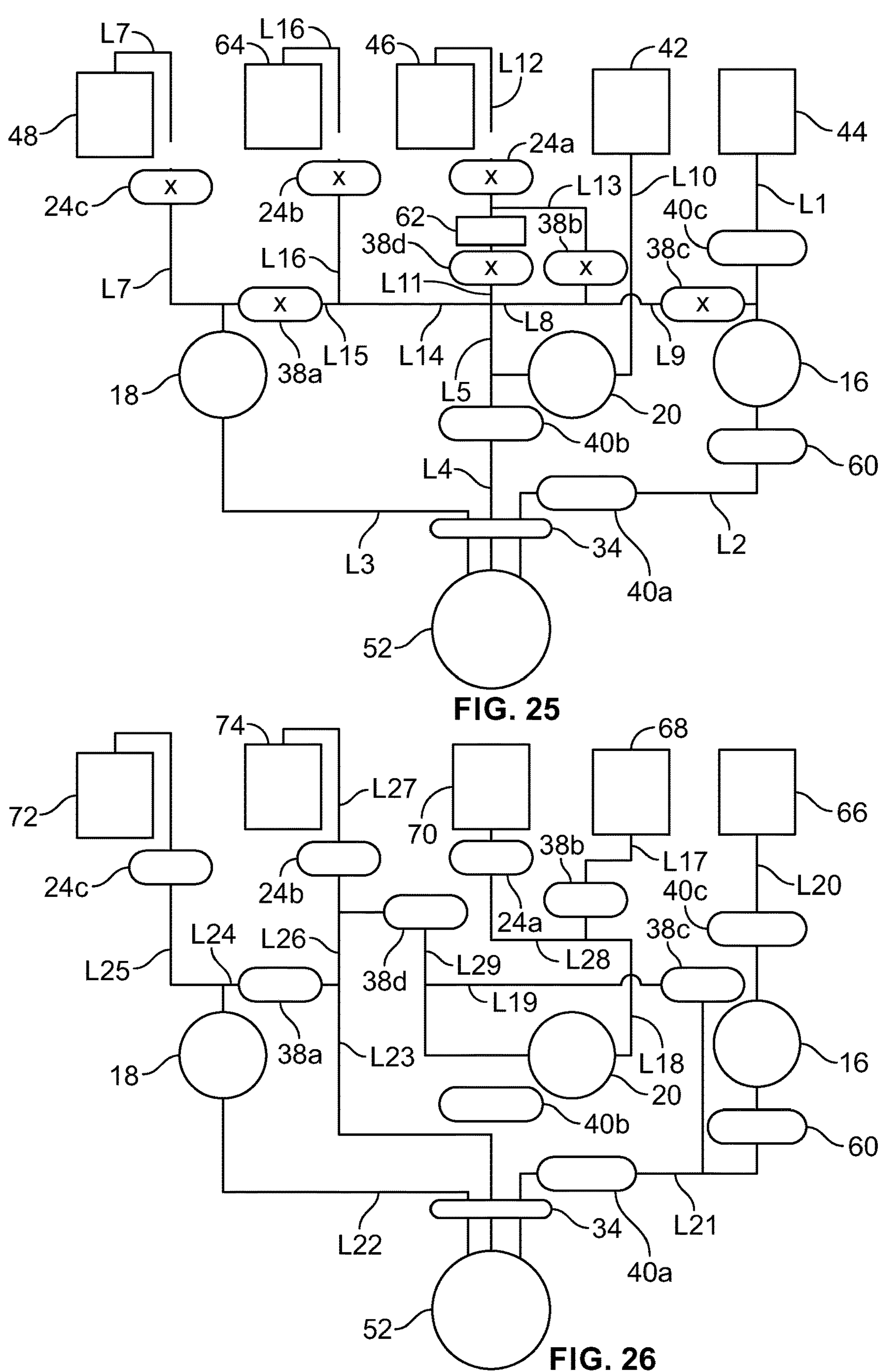
FIG. 25 is a schematic view of the blood processing system of FIG. 14 executing a "sealing" stage of an exemplary blood processing procedure.
FIG. 26 is a schematic view of another embodiment of a fluid flow circuit mounted to the processing device of FIG. 1 to complete a blood processing system according to an aspect of the present disclosure.

The air evacuation stage will continue until all of the air is removed from the red blood cell collection container 46. Upon completion of the air evacuation stage, any of a number of post-processing stages may be executed. For example, FIG. 25 shows a "sealing" stage in which all of the clamps and valves are closed and all of the pumps are deactivated. The line L12 connected to the red blood cell collection container 46, the line L7 connected to the plasma collection container 48, and the line L16 connected to the buffy coat collection container 64 are sealed and optionally severed for storage of the plasma, red blood cell, and buffy coat products. While it is possible to remove air from the buffy coat collection container 64 (e.g., using a variation of the air evacuation stage of FIG. 24) before sealing line L16, doing so is typically not necessary, as it is most common for the collected buffy coat to be pooled with other buffy coats, with the pooled buffy coats being processed to create a platelet product.

Red Blood Cell Product Washing

One possible post-processing stage is "washing" of the red blood cell product. Red blood cells are often stored for long periods of time prior to transfusion. In this case, the cells are commonly "washed" prior to transfusion to remove the supernatant suspension (and, thus, any undesirable extracellular substances) from the cells while maintaining the integrity and functionality of the cells, thereby decreasing the probability of immunological reaction in a recipient.

FIG. 26 shows an exemplary fluid flow circuit (along with selected components of the processing device 10) for washing a red blood cell product, with FIGS. 27-37 showing different stages of an exemplary red blood cell washing procedure. It should be understood that the fluid flow circuit and the procedure of FIGS. 26-37 are merely exemplary and that a fluid flow circuit and procedure for washing red blood cells may be differently configured without departing from the scope of the present disclosure. It should also be understood that the method may be carried out using pre-configured parameters or may be configurable to enable the user to customize their own washing protocols, with the procedure described herein exemplifying a standard pre-configured washing process.

The fluid flow circuit of FIG. 26 includes a red blood cell source container 66. In one embodiment, a sealed red blood cell collection container 46 obtained using one of the procedures described herein may be connected to a separate fluid flow circuit to provide a source container 66. In another embodiment, the red blood cells may be conveyed out of the red blood cell collection container 46 and into a red blood cell source container 66 of a separate fluid flow circuit. However, it should be understood that the washing procedure described herein is not limited to red blood cells obtained according to one of the procedures described herein, but rather the red blood cells to be washed may be variously obtained without departing from the scope of the present disclosure.

Figures 27, 28:
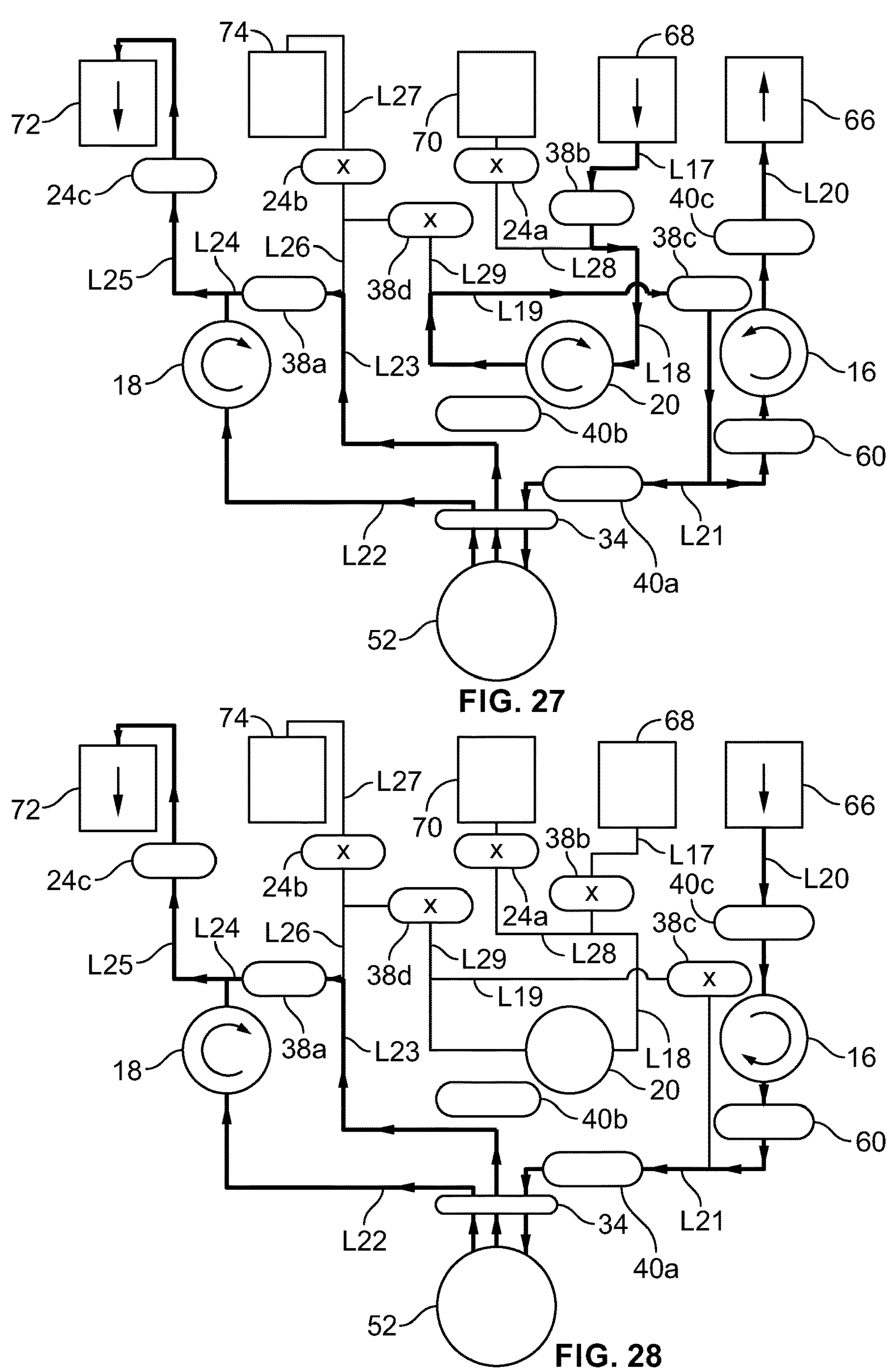
FIG. 27 is a schematic view of the blood processing system of FIG. 26 executing a "solution prime" stage of an exemplary blood processing procedure.
FIG. 28 is a schematic view of the blood processing system of FIG. 26 executing a "blood prime" stage of an exemplary blood processing procedure, without red blood cell dilution.
Figures 29, 30:
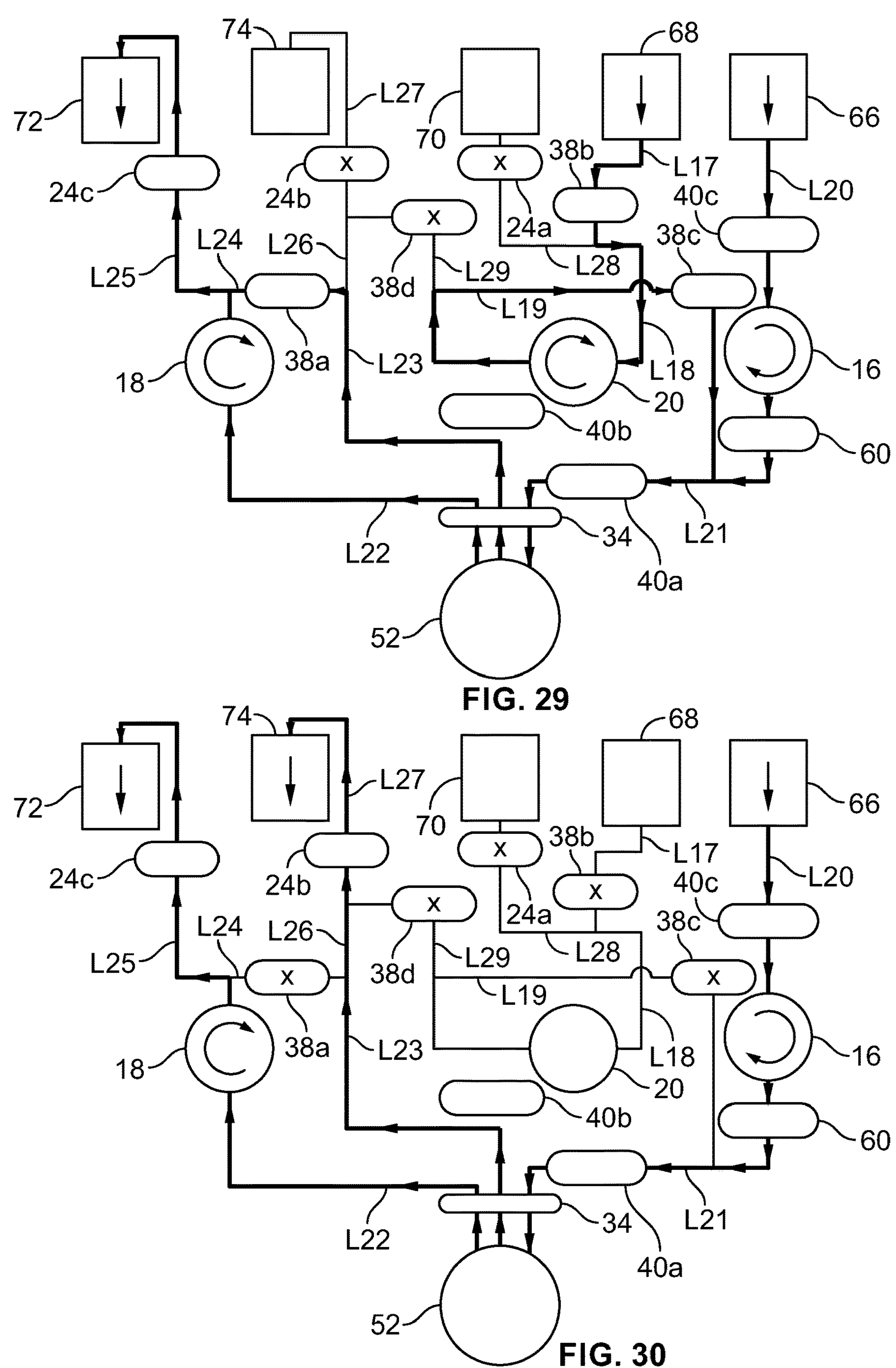
FIG. 29 is a schematic view of a variation of the "blood prime" stage of FIG. 28 in which red blood cells are diluted using a pre-wash solution.
FIG. 30 is a schematic view of the blood processing system of FIG. 26 executing a "washing" stage of an exemplary blood processing procedure, without red blood cell dilution.

The illustrated procedure begins with a priming stage in which the fluid flow circuit is primed using either a wash solution (FIG. 27) or the stored red blood cells (FIGS. 28 and 29). The phase of FIG. 27 is referred to herein as a "solution prime" stage. This is an optional stage, as the system is capable of functioning without a solution prime, instead priming the fluid flow circuit using only red blood cells from the red blood cell source container 66, as will be described below (and as shown in FIGS. 28 and 29). Application of a solution prime stage may be dependent on any of a number of factors, including: user preference, the quality of the red blood cell product, the type of solution employed, and the particular configuration of the fluid flow circuit. Prior to beginning a procedure, the operator may be presented with the option of executing an initial solution prime stage or instead beginning by priming the fluid flow circuit using stored red blood cells.

The illustrated fluid flow circuit includes two solution containers 68 and 70, with the solutions stored within the two containers 68 and 70 (with the solutions collectively referred to herein as "wash solutions" and the containers collectively referred to herein as "wash solution containers") being the same or different. In the procedure described herein, the two wash solutions are different and are used during different stages of the procedure. The solution stored in wash solution container 68 (which solution is referred to herein as a "pre-wash solution" and which container is referred to herein as the "pre-wash solution container") is used for diluting the red blood cells prior to washing (as will be described) and for priming the fluid flow circuit, if the solution prime stage is executed. In an exemplary embodiment, the pre-wash solution may be saline, though it should be understood that other fluids may be employed as a pre-wash solution without departing from the scope of the present disclosure. As for the solution stored in wash solution container 70 (which solution is referred to herein as a "post-wash solution" and which container is referred to herein as the "post-wash solution container"), it may be used for dilution or storage of the final washed red blood cell product. In an exemplary embodiment, the post-wash solution may be ADSOL®, though it should be understood that other fluids (e.g., some other red blood cell additive solution) may be employed as a post-wash solution without departing from the scope of the present disclosure.

If a solution prime stage is desired, valve 38*b* is opened and the pre-wash solution is drawn from the pre-wash solution container 68 and into line L17 by pump 20 (which is referred to in describing this procedure as the "wash solution pump"). Clamp 24*a* is closed, which directs the pre-wash solution into line L18. Valve 38*d* is closed, while valve 38*c* is open, which directs the pre-wash solution from line L18 into line L19 and to the junction of lines L19, L20, and L21.

Pump 16 (which is referred to in describing this procedure as the "source pump") and pump 18 (which is referred to in describing this procedure as the "waste pump") are both active during the solution prime stage, which causes portions of the pre-wash solution to be directed from line L19 into lines L20 and L21. The portion of the pre-wash solution directed into line L20 flows through the air trap 60 and pressure sensor 40*c* to the red blood cell source container 66, while the portion of the pre-wash solution directed into line L21 flows through the pressure sensor 40*a* and the optical sensor 34 and into the processing chamber 52 (which is positioned within the centrifuge 22 of the processing device 10). The percentages of the pre-wash solution directed into lines L20 and L21 will depend on the relative rates of pumps 16 and 18. Typically, the waste pump 18 will be operated at a higher rate than the source pump 18 to direct more pre-wash solution into line L21 than into L20, which may be advantageous due to there tending to be more air to be cleared from the path traversed by the pre-wash solution flowing into line L21.

As in the above-described blood prime stages, the centrifuge 22 may be stationary during the solution prime stage or may instead be controlled by the controller of the processing device 10 to spin at a low rotation rate (e.g., on the order of approximately 1,000-2,000 rpm). As explained above, it may be advantageous for the centrifuge 22 to rotate during the blood prime stage in order to create enough g-force to ensure that the air in the processing chamber 52 (which includes air already present in the processing chamber 52, along with air moved into the processing chamber 52 from lines L17, L18, L19, and/or L21 by the flow of pre-wash solution) is forced towards the low-g wall of the processing chamber 52. However, as also explained above, higher centrifuge rotation rates may be undesirable, as air blocks are more likely at higher g-forces.

The pre-wash solution entering the processing chamber 52 will move towards the high-g wall of the processing chamber 52, displacing air towards the low-g wall. A supernatant outlet port of the processing chamber 52 (which corresponds to the outlet port referred to as the "plasma outlet port" in describing the above procedures) is associated with the low-g wall of the processing chamber 52, such that most of the air will exit the processing chamber 52 via the supernatant outlet port and associated line L22, although some air may also exit the processing chamber 52 via a red blood cell outlet port associated with the high-g wall of the processing chamber 52.

Valve 38*a* is open, while clamp 24*b* is closed, which directs the air exiting the processing chamber 52 via the red blood cell outlet port through associated line L23, through line L24, and to a junction with line L22. At the junction, the air flowing through line L24 will meet up with the air flowing through line L22 (i.e., the air that exits the processing chamber 52 via the supernatant outlet port). The combined air will flow through line L25 and open clamp 24*c*, into waste container 72.

The flow of air out of the processing chamber 52 via either outlet port is monitored by the optical sensor 34, which is capable of determining the optical density of the fluid flowing through the monitored lines and discerning between air and a non-air fluid in lines L22 and L23. When a non-air fluid is detected in both lines L22 and L23 and when the portion of the pre-wash solution directed into line L20 is detected to have reached the red blood cell source container 66 (e.g., by a small increase in the weight measured by an associated weight scale), the controller of the processing device 10 will end the solution prime stage and move on to the next stage of the procedure. If one portion of the fluid flow circuit is primed before the other, the pump 16, 18 associated with the primed portion of the fluid flow circuit may be deactivated until the end of the solution prime stage.

FIGS. 28 and 29 illustrate two variations of a "blood prime" stage. While the illustrated stages are referred to as "blood prime" stages, it will be seen that the fluid flow circuit is primed using the red blood cell product, rather than whole blood. In the variation of FIG. 28, the fluid flow circuit is primed using the red blood cell product without the addition of pre-wash solution to the red blood cell product upstream of the processing chamber 52, while FIG. 29 illustrates a variation in which the fluid flow circuit is primed using the red blood cell product, with pre-wash solution being added to the red blood cell product upstream of the processing chamber 52, which will dilute the supernatant and tend to improve the percent washout. The variation of FIG. 28 may be advantageous if the objective of the procedure is simply to volume reduce the product, whereas the variation of FIG. 29 may be advantageous if washing out a contaminant is an objective of the procedure. Prior to beginning the procedure, the operator may be presented with the option of diluting the red blood cell product during the blood prime stage.

In both variations, red blood cells are drawn into the fluid flow circuit from the red blood cell source container 66 via line L20 by operation of the source pump 16. The red blood cells pass through pressure sensor 40*c* and air trap 60 before reaching the junction of lines L19, L20, and L21. In the embodiment of FIG. 28, valve 38*c* is closed, which directs the red blood cells into line L21 and through pressure sensor 40*a* and optical sensor 34 before flowing into the processing chamber 52. In the embodiment of FIG. 29, valve 38*c* is open, along with valve 38*b*, while clamp 24*a* and valve 38*d* are closed. The wash solution pump 20 operates to draw pre-wash solution from the pre-wash solution container 68 via line L17, through lines L18 and L19, and to the junction of lines L19, L20, and L21, where the pre-wash solution is mixed with the red blood cells being pumped through line L20. The diluted red blood cells flow through line L21, pressure sensor 40*a*, and optical sensor 34 before flowing into the processing chamber 52.

The rotation rate of the centrifuge 22 may depend on whether the solution prime stage was executed. If the solution prime stage was not executed, the centrifuge 22 may be stationary during the blood prime stage or may instead be controlled by the controller of the processing device 10 to spin at a low rotation rate (e.g., on the order of approximately 1,000-2,000 rpm), with a low rotation rate being advantageous for the reasons described above. On the other hand, if the solution prime stage has been executed, the centrifuge 22 may be controlled to operate at a greater rotation rate (e.g., on the order of 4,500-5,000 rpm), which may be equal to the rotation rate during a subsequent "washing" stage (which will be described in greater detail). As explained above, a greater rotation rate may be less desirable when priming the fluid flow circuit due to the greater likelihood of air blocks, though the risk is mitigated by first performing the solution prime stage, as the red blood cells flowing into the processing chamber 52 will displace wash solution, rather than air.

The (diluted or undiluted) red blood cells entering the processing chamber 52 will move towards the high-g wall of the processing chamber 52, displacing air (if the blood prime stage is the initial stage) or wash solution (if the blood prime stage follows a solution prime stage) towards the low-g wall. Most of the air (or wash solution) will exit the processing chamber 52 via the supernatant outlet port and associated line 122, although some air (or wash solution) may also exit the processing chamber 52 via the red blood cell outlet port and associated line 123. Valve 38*a* is open, while clamp 24*b* is closed, which directs the air (or wash solution) exiting the processing chamber 52 via the red blood cell outlet port through associated line L23, through line L24, and to the junction with line L22. At the junction, the air (or wash solution) flowing through line L24 will meet up with the air (or wash solution) flowing through line L22 (i.e., the air or wash solution that exits the processing chamber 52 via the supernatant outlet port). The combined air (or wash solution) will flow through line L25 and open clamp 24*c*, into waste container 72. The flow of fluid out of the processing chamber 52 via the outlet ports is monitored by the optical sensor 34 to determine when to end the blood prime stage.

After the fluid flow circuit has been primed, the procedure advances to a "washing" stage in which the red blood cells are centrifuged to remove the supernatant suspension from the cells. The centrifuge 22 is operated at a rate that is sufficient to separate the red blood cell product into washed red blood cells and supernatant, which may be in the range of approximately 4,500 to 5,500 rpm, for example. As described above, the centrifuge 22 may be operating at a relatively low rotation rate during the blood prime stage if the solution prime stage is omitted, in which case the rotation rate of the centrifuge 22 is increased upon transitioning to the washing stage. As also described above, the centrifuge 22 may be operating at a relatively high rotation rate during the blood prime stage if the solution prime stage has been executed, in which case the rotation rate of the centrifuge 22 may remain the same upon transitioning to the washing stage.

Figures 31, 32:
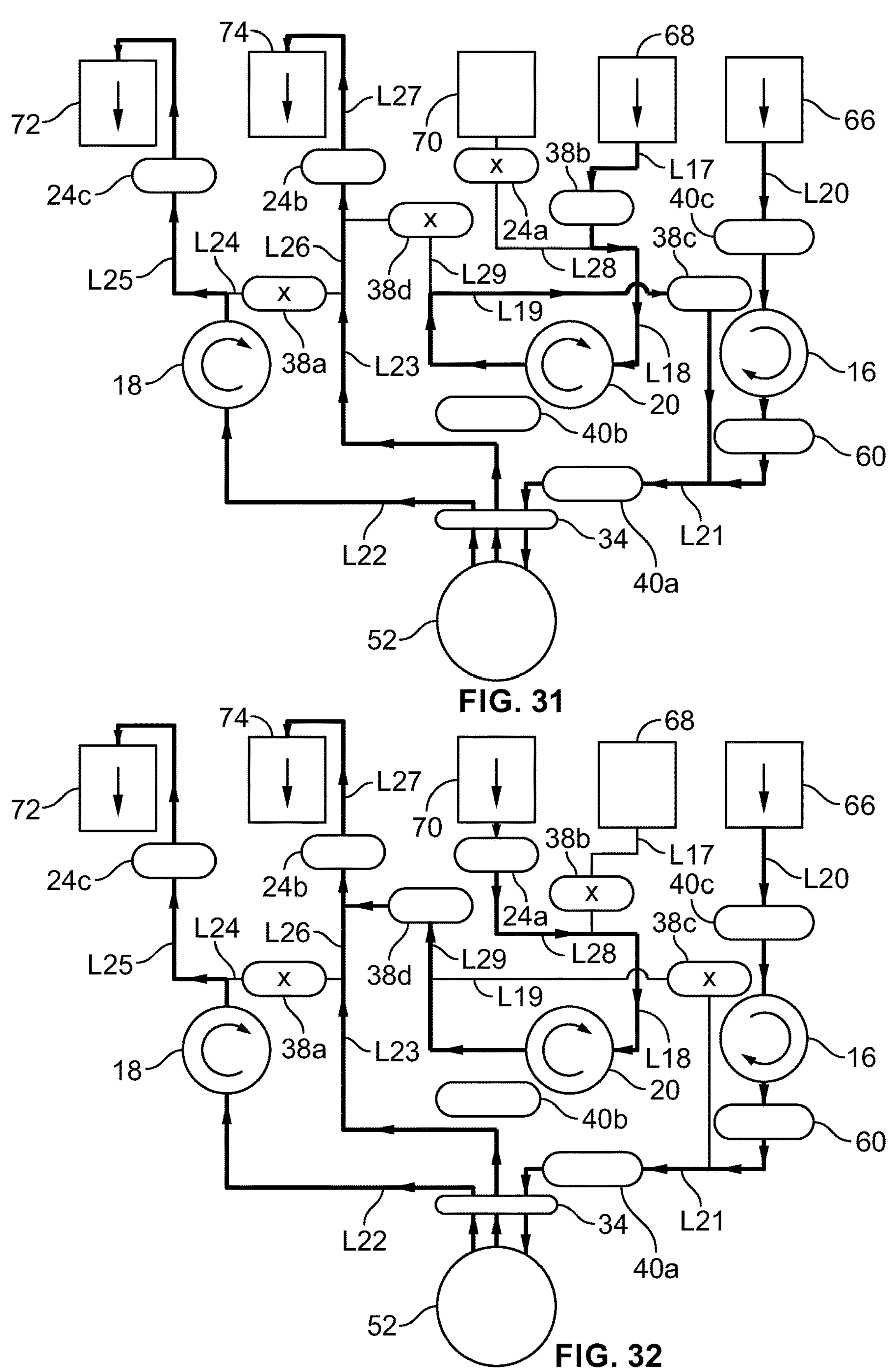
FIG. 31 is a schematic view of a variation of the "washing" stage of FIG. 30 in which red blood cells are diluted using a pre-wash solution.
FIG. 32 is a schematic view of another variation of the "washing" stage of FIG. 30 in which washed red blood cells are diluted using a post-wash solution.

FIGS. 30-32 illustrate three variations of the washing stage, with FIG. 30 illustrating an embodiment in which the red blood cells are not diluted, FIG. 31 illustrating an embodiment in which a wash solution is added to the red blood cells upstream of the processing chamber 52 (to dilute the supernatant and improve the percent washout), and FIG. 32 illustrating an embodiment in which the washed red blood cells are mixed with a wash solution after exiting the processing chamber 52 (to "volume up" the washed red blood cells). The variation of FIG. 30 may be advantageous if the objective of the procedure is simply to volume reduce the product, whereas the variation of FIG. 31 may be advantageous if washing out a contaminant is an objective of the procedure. The variation of FIG. 32 may be advantageous if additional storage is required. The variation of FIG. 32 may be used in combination with one of the other variations, which may include beginning the washing stage in the variation of FIG. 30 before transitioning to the variation of FIG. 32 (to begin "voluming up" the washed red blood cells) or by rapidly switching between the variations of FIGS. 31 and 32 throughout the washing stage (to dilute the supernatant and "volume up" the washed red blood cells).

The procedure may transition from either variation of the blood prime stage to any of the variations of the washing stage, though it may be most typical for there to be a transition from a particular blood prime stage to a particular washing stage. For example, if the red blood cells are not diluted during the blood prime stage (as in FIG. 28), it may be most typical to transition to a washing stage in which the red blood cells are not diluted upstream of the processing chamber 52 (e.g., as in FIG. 30 or 32). Similarly, if the red blood cells are diluted during the blood prime stage (as in FIG. 29), it may be most typical for upstream dilution to continue during the washing stage (as in FIG. 31). Prior to beginning a procedure, an operator may be given the choice of which variation of the washing stage to employ, which may include a combination of the variation of FIG. 32 and one of the variations of FIGS. 30 and 31. In another embodiment, the controller may determine which variations of the blood prime stage and the washing stage to employ based on input provided by the operator and proceed to carry out the procedure accordingly or, alternatively, provide recommendations to the operator based on the input.

In the embodiment of FIG. 30, red blood cells are drawn into the fluid flow circuit from the red blood cell source container 66 via line L20 by operation of the source pump 16. The red blood cells pass through pressure sensor 40*c* and air trap 60 before reaching the junction of lines L19, L20, and L21. Valve 38*c* is closed, which directs the red blood cells into line L21 and through pressure sensor 40*a* and optical sensor 34 before flowing into the processing chamber 52.

In the processing chamber 52, the supernatant suspension is separated from the red blood cells. In one embodiment, the above-described optical system comprising the laser 30 and the photodetector 32 (FIG. 1) may be employed to locate and control the position of the interface between the supernatant suspension and the red blood cells within the centrifuge 22. Alternatively, a differently configured system may be employed to monitor the separation process and ensure that it is proceeding as desired. For example, the optical sensor 34 may monitor outlet lines L22 and L23 to ensure that the separated fluid components are exiting the processing chamber 52 via the proper outlets.

The supernatant suspension exits the processing chamber 52 via the supernatant outlet port (and associated line L22), while the washed red blood cells exit the processing chamber 52 via the red blood cell outlet port (and associated line L23). Valves 38*a* and 38*d* are closed, while clamps 24*b* and 24*c* are open, which directs the supernatant to the waste container 72 (via lines L22 and L25) and directs the washed red blood cells to a washed red blood cell container 74 (via lines L23, L26, and L27). There is no pump associated with line L23, such that the washed red blood cells exit the processing chamber 52 at a rate that is equal to the difference between the rate of the source pump 16 and the rate of the waste pump 18. In alternative embodiments, there may be a pump associated with the red blood cell outlet line instead of the supernatant outlet line or a first pump associated with the supernatant outlet line and a second pump associated with the red blood cell outlet line.

The variation of FIG. 31 begins similarly to the variation of FIG. 30, with red blood cells being drawn to the junction of lines L19, L20, and L21 by operation of the source pump 16. Rather than valve 38*c* being closed (as in FIG. 30), valve 38*c* is open, along with valve 38*b*, while clamp 24*a* and valve 38*d* are closed. The wash solution pump 20 operates to draw pre-wash solution from the pre-wash solution container 68 via line L17, through lines L18 and L19, and to the junction of lines L19, L20, and L21, where the pre-wash solution is mixed with the red blood cells being pumped through line L20. The diluted red blood cells flow through line L21, pressure sensor 40*a*, and optical sensor 34 before flowing into the processing chamber 52.

As in the embodiment of FIG. 30, the supernatant suspension is separated from the red blood cells in the processing chamber 52, with the supernatant suspension (which includes the pre-wash solution) exiting the processing chamber 52 via the supernatant outlet port (and associated line L22) and the washed red blood cells exiting the processing chamber 52 via the red blood cell outlet port (and associated line L23). Valve 38*a* is closed, while clamps 24*b* and 24*c* are open, which directs the supernatant to the waste container 72 (via lines L22 and L25) and directs the washed red blood cells to the washed red blood cell container 74 (via lines L23, L26, and L27).

The variation of FIG. 32 begins similarly to the variation of FIG. 30, with red blood cells being drawn from the red blood cell source container 66 and into the processing chamber 52, where the supernatant suspension is separated from the red blood cells and directed into the waste container 72. As in FIG. 30, the washed red blood cells exit the processing chamber 52 via the red blood cell outlet port and flow through associated line L23 and into line L26. Unlike the embodiment of FIG. 30, valve 38*d* is open, along with clamp 24*a*. Valves 38*b* and 38*c* are closed, while the wash solution pump 20 is operated to draw post-wash solution from the post-wash solution container 70 via line L28, through lines L18 and L29, and to the junction of lines L26 and L29. At the junction, the post-wash solution is mixed with the washed red blood cells flowing through line L26, with the mixture flowing into line L27 and into the washed red blood cell container 74. While FIGS. 31 and 32 show different wash solutions being used before and after the red blood cells are washed, it should be understood that the same wash solution may be used as a pre-wash solution and as a post-wash solution.

Regardless of which variation of the washing stage is executed, the washing stage will end when the red blood cell source container 66 is empty, with different approaches possibly being employed to determine when the red blood cell source container 66 is empty. For example, in one embodiment, pressure sensor 40*c* monitors the hydrostatic pressure of the red blood cell source container 66. An empty red blood cell source container 66 may be detected when the hydrostatic pressure measured by pressure sensor 40*c* is at or below a threshold value. Alternatively (or additionally), the weight of the red blood cell source container 66 may be monitored by a weight scale, with an empty red blood cell source container 66 being detected when the weight is at or below a threshold value.

Figures 33, 34:
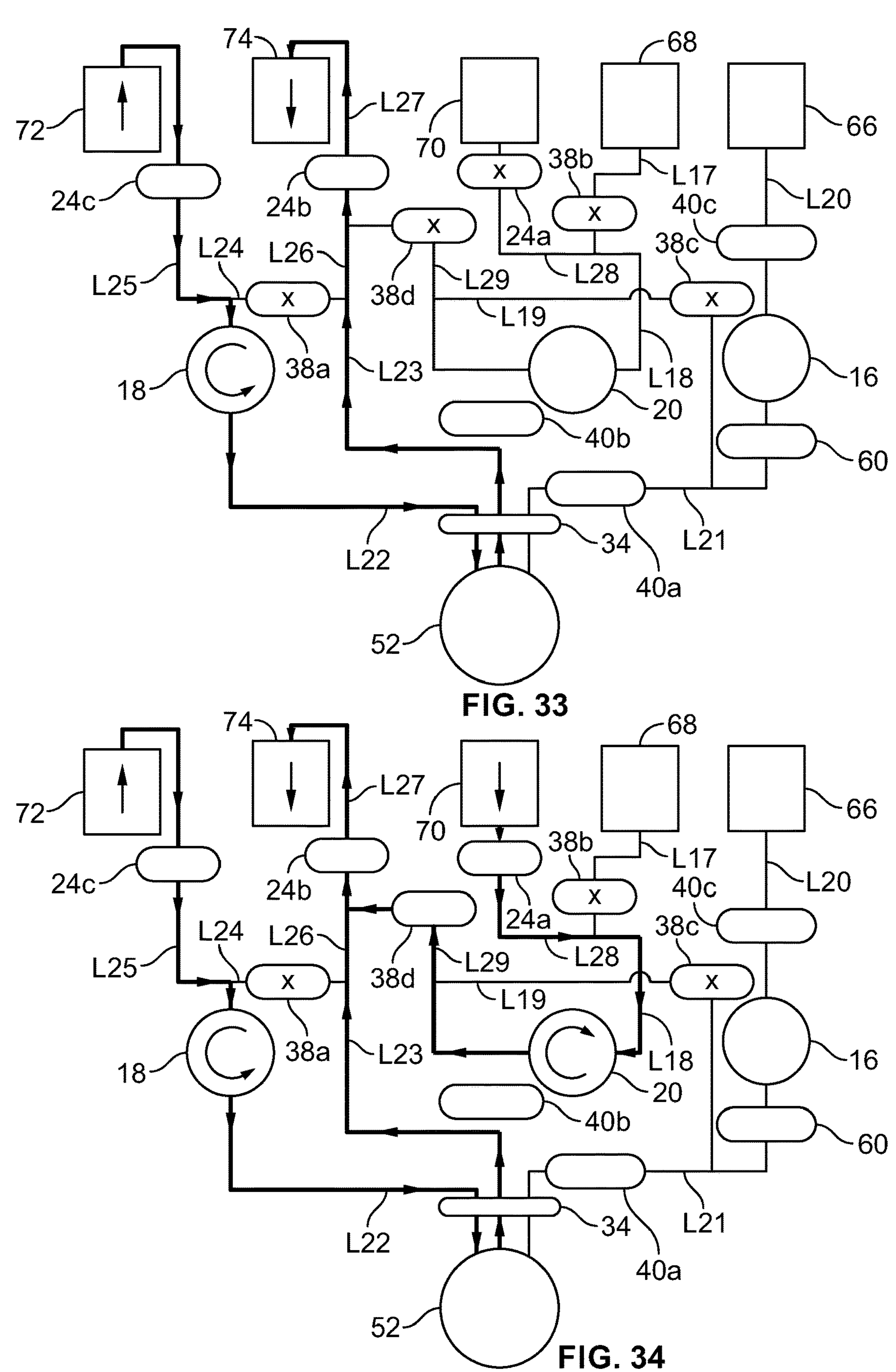
FIG. 33 is a schematic view of the blood processing system of FIG. 26 executing a "red blood cell recovery" stage of an exemplary blood processing procedure, without red blood cell dilution.
FIG. 34 is a schematic view of a variation of the "red blood cell recovery" stage of FIG. 33 in which washed red blood cells are diluted using a post-wash solution.

Once the red blood cell source container 66 is empty, the procedure will transition to a "red blood cell recovery" stage in which air from the waste container 72 (which was conveyed there during the priming stage(s)) is used to recover washed red blood cells from the processing chamber 52. FIGS. 33 and 34 illustrate two variations of the red blood cell recovery stage, with FIG. 33 illustrating an embodiment in which the red blood cells in the processing chamber 52 are flushed into the washed red blood cell container 74 without further dilution and FIG. 34 illustrating an embodiment including additional dilution of the washed red blood cells using a wash solution.

The procedure may transition from any variation of the washing stage to either variation of the red blood cell recovery stage, though it may be most typical for there to be a transition from a particular washing stage to a particular red blood cell recovery stage. For example, if the washed red blood cells are not being diluted at the end of the washing stage (as in FIGS. 30 and 31), it may be most typical to transition to a red blood cell recovery stage in which the washed red blood cells are not diluted downstream of the processing chamber 52 (as in FIG. 33). Similarly, if the washed red blood cells are being diluted at the end of the washing stage (as in FIG. 32), it may be most typical for downstream dilution to continue during the red blood cell recovery stage (as in FIG. 34). Prior to beginning a procedure, an operator may be given the choice of which variation of the red blood cell recovery stage to employ, which may include a combination of the two variations (e.g., transitioning from the variation of FIG. 34 to the variation of FIG. 33 once sufficient wash fluid has been conveyed into the washed red blood cell container 74). In another embodiment, the controller may determine which variation(s) of the red blood cell recovery stage to employ based on input provided by the operator and proceed to carry out the procedure accordingly or, alternatively, provide recommendations to the operator based on the input.

In both variations, the source pump 16 is deactivated, while the waste pump 18 is operated in a reverse direction (with respect to its direction of operation up to this stage of the procedure). This draws the air from the waste container 72 and into line L25. Valve 38*a* remains closed, which directs the air through line L25, into and through line L22, and into the processing chamber 52 via the supernatant outlet port. On account of the air flowing through the supernatant outlet port, it will enter the processing chamber 52 at the low-g side. As additional air is introduced into the processing chamber 52, it will move from the low-g wall towards the high-g wall, thus displacing any liquid content through the red blood cell outlet port at the high-g side, through line L23, and into line L26. During this stage, the centrifuge 22 may be operated at a slower rate (e.g., in the range of approximately 1,000-2,000 rpm) to decrease the risk of an air blockage (as during the priming stage).

In the variation of FIG. 33, valve 38*d* is closed, while clamp 24*b* is open, which directs the recovered red blood cells into and through line L27 and into the washed red blood cell container 74. In the variation of FIG. 34, valve 38*d* is open, along with clamp 24*a*, while valves 38*c* and 38*d* are closed. The wash solution pump 20 operates to draw post-wash solution from the post-wash solution container 70 via line L28, through lines L18 and L29, and to the junction of lines L26 and L29. At the junction, the post-wash solution is mixed with the recovered red blood cells flowing through line L26, with the mixture flowing into line L27 and into the washed red blood cell container 74. While FIG. 34 shows the washed red blood cells being diluted using a different wash solution from the one used to (optionally) prime the fluid flow circuit, it should be understood that the same wash solution may be used for both.

The red blood cell recovery stage may continue until the optical sensor 34 detects air exiting the red blood cell outlet port, until all of the air has been removed from the waste container 72 (e.g., as determined by a weight scale associated with the waste container 72), or until a predetermined volume has been displaced. Other approaches may also be employed to determine when to end the red blood cell recovery stage without departing from the scope of the present disclosure.

Figures 35, 36:
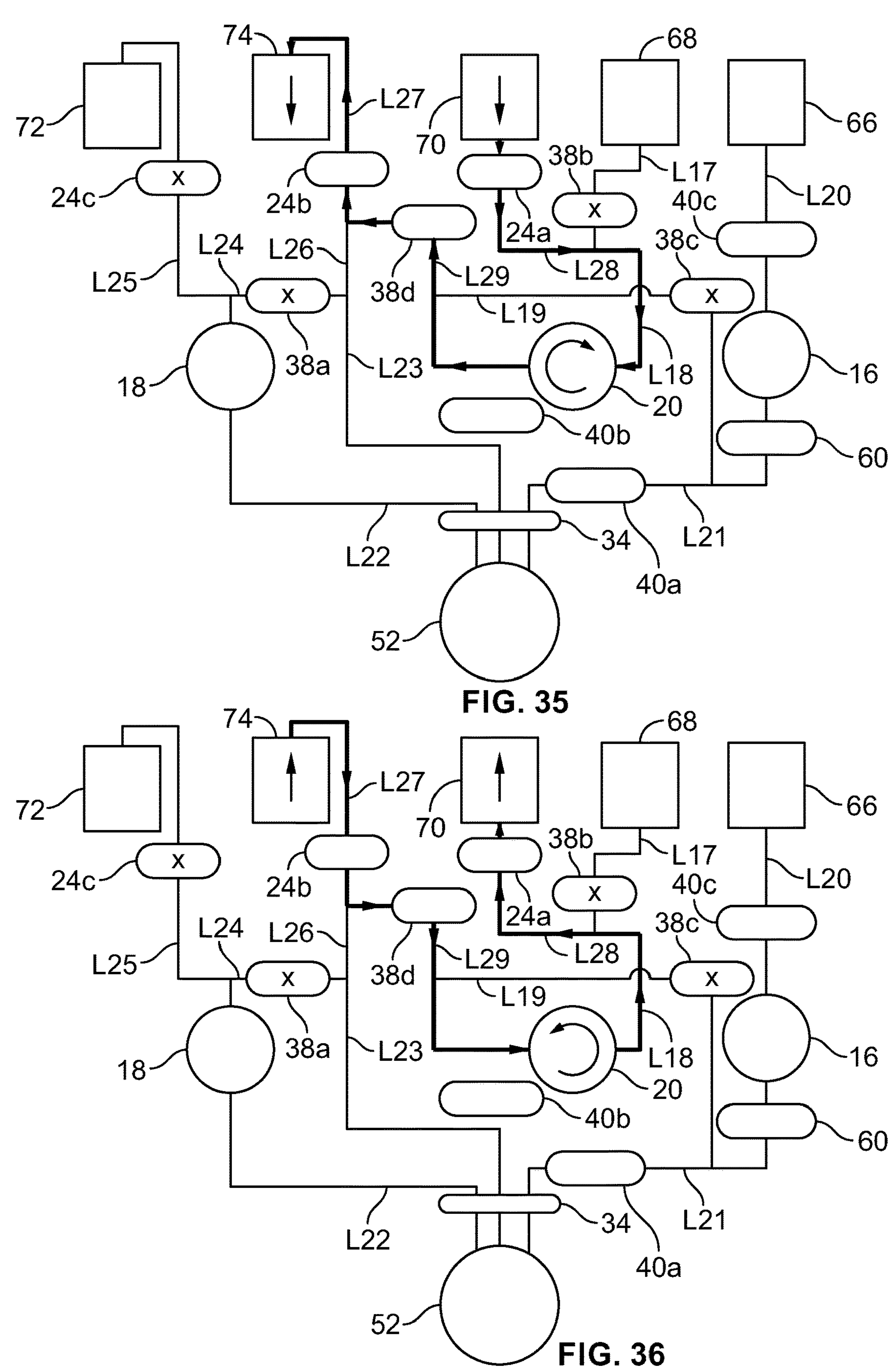
FIG. 35 is a schematic view of the blood processing system of FIG. 26 executing a "dilution" stage in which washed red blood cells are diluted using a post-wash solution.
FIG. 36 is a schematic view of the blood processing system of FIG. 26 executing an "air evacuation" stage of an exemplary blood processing procedure.

An optional "dilution" stage follows the red blood cell recovery stage. During the dilution stage, wash solution is added to the washed red blood cells in the washed red blood cell container 74 until a target amount of wash solution has been added into the washed red blood cell container 74. If sufficient wash solution has already been added during the washing and/or red blood cell recovery stages, then the dilution stage may be unnecessary. On the other hand, if additional dilution is required (which may be most typical if the wash solution pump 20 was used during earlier stages of the procedure to dilute the supernatant prior to the red blood cells entering the processing chamber 52), the dilution stage may be necessary. FIG. 35 shows an exemplary dilution stage in which the washed red blood cells are diluted using a different wash solution from the one used to (optionally) prime the fluid flow circuit, but it should be understood that the same wash solution may be used for both or for wash solution from both wash solution containers 68 and 70 to be used.

In the embodiment of FIG. 35, valve 38*b* and 38*c* remain closed, while clamp 24*a* and valve 38*d* are opened (if not already open during the red blood cell recovery stage). Clamp 24*b* remains open, with clamp 24*c* being closed. The waste pump 18 is deactivated (if not already inactive during the red blood cell recovery stage), while the wash solution pump 20 is activated (if not already active during the red blood cell recovery stage) to draw post-wash solution from the post-wash solution container 70 via line L28, through lines L18, L29, and line L27 and into the washed red blood cell container 74. This may continue until a predetermined volume of wash solution has been transferred, which may be detected by a weight scale associated with any of the wash solution containers used during the dilution stage.

When the dilution stage is complete, the system will transition to an "air evacuation" stage, as shown in FIG. 36. During the air evacuation stage, the washed red blood cell container 74 is "burped" to remove all residual air for storage. This is done by reversing the direction of operation of the wash solution pump 20, which causes the wash solution pump 20 to draws air out of the washed red blood cell container 74, through line L27 and open clamp 24*b*, into line L29 and through open valve 38*d*. The air continues through line L18, line L28, and open clamp 24*a*, with the air ending up in the post-wash solution container 70. While FIG. 36 shows the air being evacuated from the washed red blood cell container 74 to the post-wash solution container 70, it is within the scope of the present disclosure for all or a portion of the air to be directed to a different location of the fluid flow circuit (e.g., into the pre-wash solution container 68 and/or into the waste container 72, if provided).

The air evacuation stage will continue until all of the air is removed from the washed red blood cell container 74, which may be determined (for example) by detecting a change in the weight of the washed red blood cell container 74 (e.g., using a weight scale).

Figure 37:
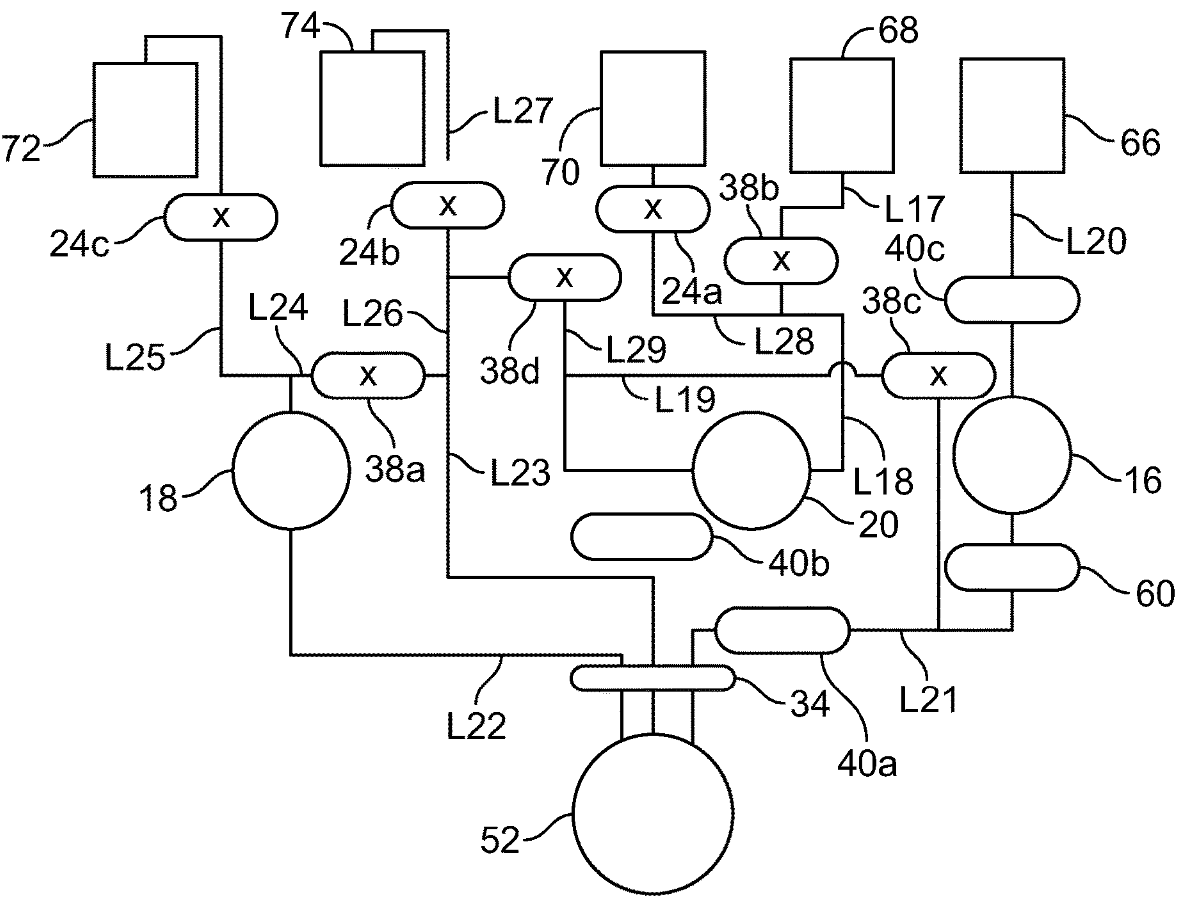
FIG. 37 is a schematic view of the blood processing system of FIG. 26 executing a "sealing" stage of an exemplary blood processing procedure.

Upon completion of the air evacuation stage, any of a number of post-processing stages may be executed. For example, FIG. 37 shows a "sealing" stage in which all of the clamps and valves are closed and all of the pumps are deactivated. The line L27 connected to the washed red blood cell collection container 74 is sealed and optionally severed for storage of the washed red blood cells. If line L27 is severed, the washed red blood cell container 74 may be stored, while the remainder of the fluid flow circuit is disposed of. Lines L27 may be sealed (and optionally severed) according to any suitable approach, which may include being sealed by an RF sealer incorporated or associated with clamp 24*b*, for example. In another embodiment, the fluid flow circuit may be removed from the processing device 10, with line L27 being sealed (and optionally severed) using a dedicated sealing device.

Aspects

Aspect 1. A blood processing system, comprising: a reusable processing device including a pump system, a valve system, a centrifuge, and a controller; and a disposable fluid flow circuit including a processing chamber received by the centrifuge, a red blood cell collection container, a plasma collection container, an additive solution container, and a plurality of conduits fluidly connecting the components of the fluid flow circuit, wherein the controller is configured to execute a blood prime stage in which the pump system conveys whole blood from a blood source to the processing chamber to convey air within the fluid flow circuit into the plasma collection container, execute an establish separation stage in which the centrifuge separates the whole blood in the processing chamber into plasma and red blood cells and the pump system and the valve system cooperate to convey separated plasma and red blood cells out of the processing chamber, recombine the separated plasma and red blood cells as recombined whole blood, and convey the recombined whole blood into the processing chamber without conveying whole blood from the blood source to the processing chamber, execute a collection stage in which the pump system conveys whole blood from the blood source to the processing chamber until a total of one unit of whole blood has been conveyed from the blood source to the processing chamber, the centrifuge separates the whole blood in the processing chamber into plasma and red blood cells, and the pump system and the valve system cooperate to convey separated plasma out of the processing chamber and into the plasma collection container, to convey separated red blood cells out of the processing chamber, and to convey additive solution out of the additive solution container, with the separated red blood cells and the additive solution being combined as a mixture and conveyed into the red blood cell collection container, execute a red blood cell recovery stage in which the pump system and the valve system cooperate to convey air from the plasma collection container into the processing chamber to convey separated red blood cells out of the processing chamber and to convey additive solution out of the additive solution container, with the separated red blood cells and the additive solution continuing to be combined as the mixture and conveyed into the red blood cell collection container, execute an additive solution flush stage in which the pump system and the valve system cooperate to convey additive solution from the additive solution container to the red blood cell collection container until a target amount of additive solution has been conveyed into the red blood cell collection container, and execute an air evacuation stage in which the pump system and the valve system cooperate to convey air out of the red blood cell collection container.

Aspect 2. The blood processing system of Aspect 1, wherein the fluid flow circuit includes a whole blood container containing one unit of whole blood, and the blood source is the whole blood container.

Aspect 3. The blood processing system of Aspect 2, wherein the processing device includes a first pressure sensor configured to measure hydrostatic pressure of the whole blood container, and the controller is configured to end the collection stage based at least in part on the hydrostatic pressure of the whole blood container.

Aspect 4. The blood processing system of any one of Aspects 2-3, wherein the processing device includes a first weight scale configured to measure a weight of the whole blood container, and the controller is configured to end the collection stage based at least in part on the weight of the whole blood container.

Aspect 5. The blood processing system of Aspect 1, wherein the blood source is a living donor.

Aspect 6. The blood processing system of any one of the preceding Aspects, wherein the processing chamber is formed of a generally rigid material.

Aspect 7. The blood processing system of any one of Aspects 1-5, wherein the processing chamber is formed of a generally flexible material.

Aspect 8. The blood processing system of any one of the preceding Aspects, wherein the processing device includes an optical sensor configured to monitor fluid exiting the processing chamber, and the controller is configured to end the blood prime stage when the optical sensor detects a non-air fluid exiting the processing chamber.

Aspect 9. The blood processing system of any one of the preceding Aspects, wherein the controller is configured to control the centrifuge to remain stationary during the blood prime stage.

Aspect 10. The blood processing system of any one of Aspects 1-8, wherein the controller is configured to control the centrifuge to rotate during the blood prime stage.

Aspect 11. The blood processing system of any one of the preceding Aspects, wherein the processing device includes an interface detector configured to determine a location of an interface between separated blood components within the processing chamber, and the controller is configured to end the establish separation stage when the interface detector has determined that the interface is at a target location and when the controller has determined that steady state separation has been achieved.

Aspect 12. The blood processing system of any one of the preceding Aspects, wherein the processing device includes a leukoreduction filter, and the pump system and the valve system cooperate to convey the mixture through the leukoreduction filter before being conveyed into the red blood cell collection container during at least a portion of the collection stage.

Aspect 13. The blood processing system of Aspect 12, wherein the processing device includes a second pressure sensor configured to measure pressure of the leukoreduction filter, and the controller is configured to control the valve system to direct the mixture to the red blood cell collection container without first passing through the leukoreduction filter based at least in part on the pressure of the leukoreduction filter.

Aspect 14. The blood processing system of Aspect 13, wherein controller is configured to control the valve system to direct the mixture through the leukoreduction filter at the beginning of the red blood cell recovery stage when the mixture is being directed through the leukoreduction filter at the end of the collection stage, and control the valve system to direct the mixture to the red blood cell collection container without first passing through the leukoreduction filter during the red blood cell recovery stage when the mixture is being directed to the red blood cell collection container without first passing through the leukoreduction filter at the end of the collection stage.

Aspect 15. The blood processing system of any one of the preceding Aspects, wherein the controller is configured to control the centrifuge to operate at a slower speed during the red blood cell recovery stage than during the collection stage.

Aspect 16. The blood processing system of any one of the preceding Aspects, wherein the processing device includes a second weight scale configured to measure a weight of the plasma collection container, and the controller is configured to end the red blood cell recovery stage based at least in part on the weight of the plasma collection container.

Aspect 17. The blood processing system of any one of the preceding Aspects, wherein the processing device includes a third weight scale configured to measure a weight of the additive solution container, and the controller is configured to end the additive solution flush stage based at least in part on the weight of the additive solution container.

Aspect 18. The blood processing system of any one of the preceding Aspects, wherein the processing device includes a fourth weight scale configured to measure a weight of the red blood cell collection container, and the controller is configured to end the additive solution flush stage based at least in part on the weight of the red blood cell collection container.

Aspect 19. The blood processing system of any one of the preceding Aspects, wherein the processing device includes a fourth weight scale configured to measure a weight of the red blood cell collection container, and the controller is configured to end the air evacuation stage based at least in part on the weight of the red blood cell collection container.

Aspect 20. The blood processing system of any one of the preceding Aspects, wherein the processing device includes a sealing system, and the controller is configured to control the sealing system to seal a first conduit connected to the red blood cell collection container and to seal a second conduit connected to the plasma collection container at the end of the air evacuation stage.

Aspect 21. The blood processing system of any one of the preceding Aspects, wherein the fluid flow circuit includes a buffy coat collection container, the whole blood is separated into plasma, red blood cells, and a buffy coat between the separated plasma and the separated red blood cells within the processing chamber during the establish separation and collection stages, and the controller is configured to execute a buffy coat harvest stage after completion of the red blood cell recovery stage and before execution of the additive solution flush stage in which the pump system and the valve system cooperate to convey air from the plasma collection container into the processing chamber to convey the buffy coat out of the processing chamber and into the buffy coat collection container.

Aspect 22. The blood processing system of Aspect 21, wherein the processing device includes an optical sensor configured to monitor fluid exiting the processing chamber, and the controller is configured to end the red blood cell recovery stage when the optical sensor detects a non-red blood cell fluid exiting the processing chamber.

Aspect 23. The blood processing system of any one of Aspects 21-22, wherein the processing device includes an optical sensor configured to monitor fluid exiting the processing chamber, and the controller is configured to end the buffy coat harvest stage when the optical sensor detects a non-buffy coat fluid exiting the processing chamber.

Aspect 24. The blood processing system of any one of Aspects 21-23, wherein the processing device includes a sealing system, and the controller is configured to control the sealing system to seal a conduit connected to the buffy coat collection container at the end of the air evacuation stage.

Aspect 25. A method for processing one unit of whole blood into a red blood cell product and a plasma product, comprising: executing a blood prime stage in which whole blood is conveyed from a blood source to a processing chamber of a fluid flow circuit to convey air within the fluid flow circuit into a plasma collection container of the fluid flow circuit; executing an establish separation stage in which a centrifuge is operated to separate the whole blood in the processing chamber into plasma and red blood cells, separated plasma and red blood cells are conveyed out of the processing chamber and recombined as recombined whole blood, and the recombined whole blood is conveyed into the processing chamber without conveying whole blood from the blood source to the processing chamber; executing a collection stage in which whole blood is conveyed from the blood source to the processing chamber until a total of one unit of whole blood has been conveyed from the blood source to the processing chamber, the centrifuge is operated to separate the whole blood in the processing chamber into plasma and red blood cells, the separated plasma is conveyed out of the processing chamber and into the plasma collection container, the separated red blood cells are conveyed out of the processing chamber, and an additive solution is conveyed out of an additive solution container of the fluid flow circuit, with the separated red blood cells and the additive solution being combined as a mixture and conveyed into a red blood cell collection container of the fluid flow circuit; executing a red blood cell recovery stage in which air from the plasma collection container is conveyed into the processing chamber to convey separated red blood cells out of the processing chamber and additive solution is conveyed out of the additive solution container, with the separated red blood cells and the additive solution continuing to be combined as the mixture and conveyed into the red blood cell collection container; executing an additive solution flush stage in which additive solution is conveyed from the additive solution container to the red blood cell collection container until a target amount of additive solution has been conveyed into the red blood cell collection container; and executing an air evacuation stage in which air is conveyed out of the red blood cell collection container.

Aspect 26. The method of Aspect 25, wherein the fluid flow circuit includes a whole blood container containing one unit of whole blood, and the blood source is the whole blood container.

Aspect 27. The method of Aspect 26, wherein said executing the collection stage includes measuring hydrostatic pressure of the whole blood container, and ending the collection stage based at least in part on the hydrostatic pressure of the whole blood container.

Aspect 28. The method of any one of Aspects 26-27, wherein said executing the collection stage includes measuring a weight of the whole blood container, and ending the collection stage based at least in part on the weight of the whole blood container.

Aspect 29. The method of Aspect 25, wherein the blood source is a living donor.

Aspect 30. The method of any one of Aspects 25-29, wherein the processing chamber is formed of a generally rigid material.

Aspect 31. The method of any one of Aspects 25-29, wherein the processing chamber is formed of a generally flexible material.

Aspect 32. The method of any one of Aspects 25-31, wherein said executing the blood prime stage includes monitoring fluid exiting the processing chamber, and ending the blood prime stage when a non-air fluid is detected exiting the processing chamber.

Aspect 33. The method of any one of Aspects 25-32, wherein the centrifuge remains stationary during the blood prime stage.

Aspect 34. The method of any one of Aspects 25-32, wherein the centrifuge is rotated during the blood prime stage.

Aspect 35. The method of any one of Aspects 25-34, wherein said executing the establish separation stage includes determining a location of an interface between separated blood components within the processing chamber, and ending the establish separation stage when it has been determined that the interface is at a target location and that steady state separation has been achieved.

Aspect 36. The method of any one of Aspects 25-35, wherein said executing the collection stage includes conveying the mixture through a leukoreduction filter before being conveyed into the red blood cell collection container during at least a portion of the collection stage.

Aspect 37. The method of Aspect 36, wherein said executing the collection stage includes measuring pressure of the leukoreduction filter, and directing the mixture to the red blood cell collection container without first passing through the leukoreduction filter based at least in part on the pressure of the leukoreduction filter.

Aspect 38. The method of Aspect 37, wherein said executing the red blood cell recovery stage includes directing the mixture through the leukoreduction filter at the beginning of the red blood cell recovery stage when the mixture is being directed through the leukoreduction filter at the end of the collection stage, and directing the mixture to the red blood cell collection container without first passing through the leukoreduction filter during the red blood cell recovery stage when the mixture is being directed to the red blood cell collection container without first passing through the leukoreduction filter at the end of the collection stage.

Aspect 39. The method of any one of Aspects 25-38, wherein said executing the red blood cell recovery stage includes operating the centrifuge at a slower speed during the red blood cell recovery stage than during the collection stage.

Aspect 40. The method of any one of Aspects 25-39, wherein said executing the red blood cell recovery stage includes measuring a weight of the plasma collection container, and ending the red blood cell recovery stage based at least in part on the weight of the plasma collection container.

Aspect 41. The method of any one of Aspects 25-40, wherein said executing the additive solution flush stage includes measuring a weight of the additive solution container, and ending the additive solution flush stage based at least in part on the weight of the additive solution container.

Aspect 42. The method of any one of Aspects 25-41, wherein said executing the additive solution flush stage includes measuring a weight of the red blood cell collection container, and ending the additive solution flush stage based at least in part on the weight of the red blood cell collection container.

Aspect 43. The method of any one of Aspects 25-42, wherein said executing the air evacuation stage includes measuring a weight of the red blood cell collection container, and ending the air evacuation stage based at least in part on the weight of the red blood cell collection container.

Aspect 44. The method of any one of Aspects 25-43, further comprising sealing a first conduit connected to the red blood cell collection container and sealing a second conduit connected to the plasma collection container at the end of the air evacuation stage.

Aspect 45. The method of any one of Aspects 25-44, wherein the whole blood is separated into plasma, red blood cells, and a buffy coat between the separated plasma and the separated red blood cells within the processing chamber during the establish separation and collection stages, and the method includes executing a buffy coat harvest stage after completion of the red blood cell recovery stage and before execution of the additive solution flush stage in which air from the plasma collection container is conveyed into the processing chamber to convey the buffy coat out of the processing chamber and into a buffy coat collection container.

Aspect 46. The method of Aspect 45, wherein said executing the buffy coat harvest stage includes monitoring fluid exiting the processing chamber, and ending the red blood cell recovery stage a non-red blood cell fluid is detected exiting the processing chamber.

Aspect 47. The method of any one of Aspects 45-46, wherein said executing the buffy coat harvest stage includes monitoring fluid exiting the processing chamber, and ending the buffy coat harvest stage when a non-buffy coat fluid is detected exiting the processing chamber.

Aspect 48. The method of any one of Aspects 45-47, further comprising sealing a conduit connected to the buffy coat collection container at the end of the air evacuation stage.

Aspect 49. A blood processing device, comprising: a pump system; a centrifuge; and a controller configured to actuate the pump system to convey blood from a blood source into the centrifuge, actuate the centrifuge to separate the blood in the centrifuge into plasma, red blood cells, and a buffy coat between the separated plasma and the separated red blood cells, actuate the pump system to convey the separated plasma and the separated red blood cells out of the centrifuge, and actuate the pump system to convey air into the centrifuge to convey the buffy coat out of the centrifuge for collection.

Aspect 50. The blood processing device of Aspect 49, wherein the controller is configured to control the centrifuge to operate at a slower speed when conveying the buffy coat out of the centrifuge than when conveying the separated plasma and the separated red blood cells out of the centrifuge.

Aspect 51. The blood processing device of any one of Aspects 49-50, wherein the separated plasma is conveyed out of the centrifuge via a plasma outlet, the separated red blood cells are conveyed out of the centrifuge via a red blood cell outlet, the air is conveyed into the centrifuge via the plasma outlet, and the buffy coat is conveyed out of the centrifuge via the red blood cell outlet.

Aspect 52. The blood processing device of any one of Aspects 49-51, wherein the controller is configured to continue actuating the pump system to convey air into the centrifuge until a predetermined volume of fluid has been displaced from the centrifuge.

Aspect 53. The blood processing device of any one of Aspects 49-51, further comprising an optical sensor configured to monitor fluid exiting the centrifuge, wherein the controller is configured to continue actuating the pump system to convey air into the centrifuge until the optical sensor detects a non-buffy coat fluid exiting the centrifuge.

Aspect 54. The blood processing device of any one of Aspects 49-53, wherein the blood processing device is configured for use in combination with a fluid flow circuit including a plasma collection container, the controller is configured to actuate the pump system to convey air in the fluid flow circuit into the plasma collection container prior to actuating the centrifuge to separate the blood in the centrifuge, and the controller is configured to actuate the pump system to convey at least a portion of the air in the plasma collection container into the centrifuge to convey the buffy coat out of the centrifuge for collection.

Aspect 55. A blood processing system, comprising: a reusable processing device including a pump system, a centrifuge, and a controller; and a disposable fluid flow circuit including a processing chamber received by the centrifuge, a buffy coat collection container, and a plurality of conduits fluidly connecting the components of the fluid flow circuit, wherein the controller is configured to actuate the pump system to convey blood from a blood source into the processing chamber, actuate the centrifuge to separate the blood in the processing chamber into plasma, red blood cells, and a buffy coat between the separated plasma and the separated red blood cells, actuate the pump system to convey the separated plasma and the separated red blood cells out of the processing chamber, and actuate the pump system to convey air into the processing chamber to convey the buffy coat out of the processing chamber and into the buffy coat collection container.

Aspect 56. The blood processing system of Aspect 55, wherein the controller is configured to control the centrifuge to operate at a slower speed when conveying the buffy coat out of the processing chamber than when conveying the separated plasma and the separated red blood cells out of the processing chamber.

Aspect 57. The blood processing system of any one of Aspects 55-56, wherein the separated plasma is conveyed out of the processing chamber via a plasma outlet port, the separated red blood cells are conveyed out of the processing chamber via a red blood cell outlet port, the air is conveyed into the processing chamber via the plasma outlet port, and the buffy coat is conveyed out of the processing chamber via the red blood cell outlet port.

Aspect 58. The blood processing system of any one of Aspects 55-57, wherein the controller is configured to continue actuating the pump system to convey air into the processing chamber until a predetermined volume of fluid has been displaced from the processing chamber.

Aspect 59. The blood processing system of any one of Aspects 55-57, wherein the processing device includes an optical sensor configured to monitor fluid exiting the processing chamber, and the controller is configured to continue actuating the pump system to convey air into the processing chamber until the optical sensor detects a non-buffy coat fluid exiting the processing chamber.

Aspect 60. The blood processing system of any one of Aspects 55-59, wherein the fluid flow circuit includes a plasma collection container, the controller is configured to actuate the pump system to convey air in the fluid flow circuit into the plasma collection container prior to actuating the centrifuge to separate the blood in the processing chamber, and the controller is configured to actuate the pump system to convey at least a portion of the air in the plasma collection container into the processing chamber to convey the buffy coat out of the processing chamber and into the buffy coat collection container.

Aspect 61. A method for collecting a buffy coat product, comprising: conveying blood from a blood source into a centrifuge; separating the blood in the centrifuge into plasma, red blood cells, and a buffy coat between the separated plasma and the separated red blood cells; conveying the separated plasma and the separated red blood cells out of the centrifuge; and conveying air into the centrifuge to convey the buffy coat out of the centrifuge for collection.

Aspect 62. The method of Aspect 61, wherein the centrifuge is operated at a slower speed when conveying the buffy coat out of the centrifuge than when conveying the separated plasma and the separated red blood cells out of the centrifuge.

Aspect 63. The method of any one of Aspects 61-62, wherein the separated plasma is conveyed out of the centrifuge via a plasma outlet, the separated red blood cells are conveyed out of the centrifuge via a red blood cell outlet, the air is conveyed into the centrifuge via the plasma outlet, and the buffy coat is conveyed out of the centrifuge via the red blood cell outlet.

Aspect 64. The method of any one of Aspects 61-63, wherein said conveying air into the centrifuge includes conveying air into the centrifuge until a predetermined volume of fluid has been displaced from the centrifuge.

Aspect 65. The method of any one of Aspects 61-63, wherein said conveying air into the centrifuge includes conveying air into the centrifuge until a non-buffy coat fluid is detected exiting the centrifuge.

Aspect 66. The method of any one of Aspects 61-65, further comprising conveying air into a plasma collection container prior to separating the blood in the centrifuge, wherein said conveying air into the centrifuge includes conveying at least a portion of the air in the plasma collection container into the centrifuge to convey the buffy coat out of the centrifuge for collection.

Aspect 67. A blood processing system, comprising: a reusable processing device including a pump system, a valve system, a centrifuge, and a controller; and a disposable fluid flow circuit including a processing chamber received by the centrifuge, a red blood cell source container, a washed red blood cell container, a waste container, and a plurality of conduits fluidly connecting the components of the fluid flow circuit, wherein the controller is configured to execute a priming stage in which the pump system and the valve system cooperate to convey air within the fluid flow circuit into the waste container, execute a washing stage in which the pump system and the valve system cooperate to convey red blood cells from the red blood cell source container to the processing chamber, the centrifuge separates the red blood cells into a supernatant and washed red blood cells, and the pump system and the valve system cooperate to convey the supernatant out of the processing chamber and into the waste container and to convey the washed red blood cells out of the processing chamber and into the washed red blood cell container, execute a red blood cell recovery stage in which the pump system and the valve system cooperate to convey air from the waste container into the processing chamber to convey washed red blood cells out of the processing chamber and into the washed red blood cell container, and execute an air evacuation stage in which the pump system and the valve system cooperate to convey air out of the washed red blood cell container.

Aspect 68. The blood processing system of Aspect 67, wherein the fluid flow circuit includes a wash solution container, and air within the fluid flow circuit is conveyed into the waste container using wash solution from the wash solution container during the priming stage.

Aspect 69. The blood processing system of any one of Aspects 67-68, wherein air within the fluid flow circuit is conveyed into the waste container using red blood cells from the red blood cell source container.

Aspect 70. The blood processing system of Aspect 69, wherein the fluid flow circuit includes a pre-wash solution container, and the controller is configured to control the pump system and the valve system to mix red blood cells flowing toward the processing chamber with pre-wash solution from the pre-wash solution container during the priming stage.

Aspect 71. The blood processing system of any one of Aspects 67-70, wherein the processing device includes an optical sensor configured to monitor fluid exiting the processing chamber, and the controller is configured to end the priming stage when the optical sensor detects a non-air fluid exiting the processing chamber.

Aspect 72. The blood processing system of any one of Aspects 67-71, wherein the controller is configured to control the centrifuge to remain stationary during the priming stage.

Aspect 73. The blood processing system of any one of Aspects 67-71, wherein the controller is configured to control the centrifuge to rotate during the priming stage.

Aspect 74. The blood processing system of any one of Aspects 67-73, wherein the fluid flow circuit includes a pre-wash solution container, and the controller is configured to control the pump system and the valve system to mix red blood cells flowing toward the processing chamber with pre-wash solution from the pre-wash solution container during the washing stage.

Aspect 75. The blood processing system of any one of Aspects 67-74, wherein the fluid flow circuit includes a post-wash solution container, and the controller is configured to control the pump system and the valve system to mix washed red blood cells flowing toward the washed red blood cell container with post-wash solution from the post-wash solution container during the washing stage.

Aspect 76. The blood processing system of any one of Aspects 67-75, wherein the processing device includes a first pressure sensor configured to measure hydrostatic pressure of the red blood cell source container, and the controller is configured to end the washing stage based at least in part on the hydrostatic pressure of the red blood cell source container.

Aspect 77. The blood processing system of any one of Aspects 67-76, wherein the processing device includes a first weight scale configured to measure a weight of the red blood cell source container, and the controller is configured to end the washing stage based at least in part on the weight of the red blood cell source container.

Aspect 78. The blood processing system of any one of Aspects 67-77, wherein the fluid flow circuit includes a post-wash solution container, and the controller is configured to control the pump system and the valve system to mix washed red blood cells flowing toward the washed red blood cell container with post-wash solution from the post-wash solution container during the red blood cell recovery stage.

Aspect 79. The blood processing system of any one of Aspects 67-78, wherein the controller is configured to control the centrifuge to operate at a slower speed during the red blood cell recovery stage than during the washing stage.

Aspect 80. The blood processing system of any one of Aspects 67-79, wherein the fluid flow circuit includes a wash solution container, and the controller is configured to execute a dilution stage in which the pump system and the valve system cooperate to convey wash solution from the wash solution container to the washed red blood cell container until a target amount of wash solution has been conveyed into the washed red blood cell container.

Aspect 81. The blood processing system of Aspect 80, wherein the wash solution container comprises a pre-wash solution container, and pre-wash solution from the pre-wash solution container is conveyed into the washed red blood cell container during the dilution stage.

Aspect 82. The blood processing system of Aspect 80, wherein the wash solution container comprises a post-wash solution container, and post-wash solution from the post-wash solution container is conveyed into the washed red blood cell container during the dilution stage.

Aspect 83. The blood processing system of Aspect 80, wherein the wash solution container comprises a pre-wash solution container and a post-wash solution container, and pre-wash solution from the pre-wash solution container and post-wash solution from the post-wash solution container are conveyed into the washed red blood cell container during the dilution stage.

Aspect 84. The blood processing system of any one of Aspects 67-83, wherein the processing device includes a sealing system, and the controller is configured to control the sealing system to seal a conduit connected to the washed red blood cell container at the end of the air evacuation stage.

Aspect 85. A method for washing red blood cells, comprising: executing a priming stage in which air within a fluid flow circuit is conveyed into a waste container of the fluid flow circuit; execute a washing stage in which red blood cells are conveyed to a processing chamber of the fluid flow circuit, the centrifuge separates the red blood cells into a supernatant and washed red blood cells, the supernatant is conveyed out of the processing chamber and into the waste container of the fluid flow circuit and the washed red blood cells are conveyed out of the processing chamber and into a washed red blood cell container of the fluid flow circuit; executing a red blood cell recovery stage in which air from the waste container is conveyed into the processing chamber to convey washed red blood cells out of the processing chamber and into the washed red blood cell container; and executing an air evacuation stage in which air is conveyed out of the washed red blood cell container.

Aspect 86. The method of Aspect 85, wherein said executing a priming stage includes conveying air into the waste container using wash solution from a wash solution container of the fluid flow circuit.

Aspect 87. The method of any one of Aspects 85-86, wherein said executing a priming stage includes conveying air into the waste container using red blood cells from the red blood cell source container.

Aspect 88. The method of Aspect 87, wherein said executing a priming stage includes mixing red blood cells flowing toward the processing chamber with pre-wash solution from a pre-wash solution container of the fluid flow circuit.

Aspect 89. The method of any one of Aspects 85-88, wherein said executing the priming stage includes monitoring fluid exiting the processing chamber, and ending the priming stage when a non-air fluid is detected exiting the processing chamber.

Aspect 90. The method of any one of Aspects 85-89, wherein the centrifuge remains stationary during the priming stage.

Aspect 91. The method of any one of Aspects 85-89, wherein the centrifuge is rotated during the priming stage.

Aspect 92. The method of any one of Aspects 85-91, wherein said executing a washing stage includes mixing red blood cells flowing toward the processing chamber with pre-wash solution from a pre-wash solution container of the fluid flow circuit.

Aspect 93. The method of any one of Aspects 85-92, wherein said executing a washing stage includes mixing washed red blood cells flowing toward the washed red blood cell container with post-wash solution from a post-wash solution container of the fluid flow circuit.

Aspect 94. The method of any one of Aspects 85-93, wherein said executing the washing stage includes measuring hydrostatic pressure of the red blood cell source container, and ending the washing stage based at least in part on the hydrostatic pressure of the red blood cell source container.

Aspect 95. The method of any one of Aspects 85-94, wherein said executing a washing stage includes measuring a weight of the red blood cell source container, and ending the washing stage based at least in part on the weight of the red blood cell source container.

Aspect 96. The method of any one of Aspects 85-95, wherein said executing a red blood cell recovery stage includes mixing washed red blood cells flowing toward the washed red blood cell container with post-wash solution from a post-wash solution container of the fluid flow circuit.

Aspect 97. The method of any one of Aspects 85-96, wherein said executing a red blood cell recovery stage includes operating the centrifuge at a slower speed during the red blood cell recovery stage than during the washing stage.

Aspect 98. The method of any one of Aspects 85-97, further comprising executing a dilution stage in which wash solution from a wash solution container of the fluid flow circuit is conveyed to the washed red blood cell container until a target amount of wash solution has been conveyed into the washed red blood cell container.

Aspect 99. The method of Aspect 98, wherein the wash solution container comprises a pre-wash solution container, and said executing a dilution stage includes conveying pre-wash solution from the pre-wash solution container into the washed red blood cell container.

Aspect 100. The method of Aspect 98, wherein the wash solution container comprises a post-wash solution container, and said executing a dilution stage includes conveying post-wash solution from the post-wash solution container into the washed red blood cell container.

Aspect 101. The method of Aspect 98, wherein the wash solution container comprises a pre-wash solution container and a post-wash solution container, and said executing a dilution stage includes conveying pre-wash solution from the pre-wash solution container and post-wash solution from the post-wash solution container into the washed red blood cell container.

Aspect 102. The method of any one of Aspects 85-101, further comprising sealing a conduit connected to the washed red blood cell container at the end of the air evacuation stage.

Aspect 103. A configurable automated blood component manufacturing system comprising: a durable hardware component and a single use fluid flow circuit; the durable hardware component comprising a pump station with plurality of pumps, a centrifuge mounting station and drive unit; an optical system associated with the centrifuge mounting station and drive unit, a microprocessor-based controller including a touchscreen for receiving operator input and displaying procedure parameters, hangers for suspending containers, a weight scale associated with each hanger configured to send a signal to the controller indicative of a weight of a container supported on an associated hanger, a plurality of tubing clamps, and a cassette nesting module including a plurality of valves and pressure sensors; the single use fluid flow circuit comprising a separation chamber configured to be received in the centrifuge mounting station and drive unit, a fluid flow control cassette configured to be mounted in the cassette nesting module, the cassette having external tubing loops engageable with the pumps so that fluid flow through the cassette is controlled by actuation of the pumps and valves, and a plurality of containers in fluid communication with the fluid flow cassette by a tubing segment associated with each container, one or more of the tubing segments being received in one of the tubing clamps; the controller being pre-programmed to automatically operate the system to perform one or more standard blood processing procedures selected by an operator by input to the touchscreen, and configured to be further programmed by the operator to perform additional blood processing procedures.

Aspect 104. The system of Aspect 103, wherein the controller is pre-programmed to perform one or more procedures for: production of red blood cells, plasma and buffy coat from a single unit of whole blood; buffy coat pooling, buffy coat separation into a platelet product; glycerol addition to red blood cells; red blood cell washing; platelet washing; and cryoprecipitate pooling and separation.

Aspect 105. The system of Aspect 103 in which the programmable controller is configured to receive input from the operator through the touchscreen for operating the system to perform a non-standard blood processing procedure.

Aspect 106. The system of Aspect 105 wherein the programmable controller is configured to receive input from the operator as to one or more of flow rates and centrifugation forces for the non-standard blood processing procedure.

Aspect 107. The system of Aspect 103, wherein the pre-programmed blood processing procedures operate the system at pre-set settings for flow rates and centrifugation forces, and the programmable controller is configured to receive input from the operator as to one or more of flow rates and centrifugation forces for the standard blood processing procedure to override the pre-programmed settings.

Aspect 108. The system of Aspect 107 wherein the programmable controller is further configured to receive input from the operator to initially accelerate to a first centrifugal force and/or flow rate over a first period of time and then to accelerate or decelerate to a second centrifugal force and/or flow rate over a second period of time.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A configurable automated blood component manufacturing system comprising:

a durable hardware component comprising a pump station with plurality of pumps, a centrifuge mounting station and drive unit, an optical system associated with the centrifuge mounting station and drive unit, a microprocessor-based controller including a touchscreen for receiving operator input and displaying procedure parameters, hangers for suspending containers, a weight scale associated with each hanger configured to send a signal to the controller indicative of a weight of a container supported on an associated hanger, a plurality of tubing clamps, and a cassette nesting module including a plurality of valves and pressure sensors; and a single use fluid flow circuit comprising a separation chamber configured to be received in the centrifuge mounting station and drive unit, a fluid flow control cassette configured to be mounted in the cassette nesting module, the cassette having external tubing loops engageable with the pumps so that fluid flow through the cassette is controlled by actuation of the pumps and valves, and a plurality of containers in fluid communication with the cassette by a tubing segment associated with each container, with one or more of the tubing segments configured to be received in one of the tubing clamps, wherein the controller is pre-programmed to automatically operate the system to perform one or more standard blood processing procedures selected by an operator by input to the touchscreen, with each standard blood processing procedure employing pre-programmed flow rates and centrifugation forces, and the controller is further configured to be programmed by the operator to perform non-standard blood processing procedures, including receiving input from the operator as to one or more flow rates and centrifugation forces to be employed during said non-standard blood processing procedures.

2. The system of claim 1, wherein the controller is pre-programmed to perform one or more procedures for: production of red blood cells, plasma and buffy coat from a single unit of whole blood; buffy coat pooling; buffy coat separation into a platelet product; glycerol addition to red blood cells; red blood cell washing; platelet washing;

and cryoprecipitate pooling and separation.

3. The system of claim 1, the programmable controller is configured to receive input from the operator through the touchscreen for operating the system to perform said non-standard blood processing procedures.

4. The system of claim 1, wherein the controller is configured to receive input from the operator as to one or more of flow rates and centrifugation forces for the standard blood processing procedures to override the pre-programmed flow rates and centrifugation forces.

5. The system of claim 4, wherein the programmable controller is further configured to receive input from the operator to initially accelerate to a first centrifugal force and/or flow rate over a first period of time and then to accelerate or decelerate to a second centrifugal force and/or flow rate over a second period of time.

6. The system of claim 1, wherein said plurality of containers includes a red blood cell collection container, a plasma collection container, and an additive solution container, and the controller is configured to execute a blood prime stage in which the pump station conveys whole blood from a blood source to the separation chamber to convey air within the fluid flow circuit into the plasma collection container, execute an establish separation stage in which the centrifuge mounting station and drive unit separate the whole blood in the separation chamber into plasma and red blood cells and the pump station and the plurality of valves cooperate to convey separated plasma and red blood cells out of the separation chamber, recombine the separated plasma and red blood cells as recombined whole blood, and convey the recombined whole blood into the separation chamber without conveying whole blood from the blood source to the separation chamber, execute a collection stage in which the pump station conveys whole blood from the blood source to the separation chamber until a total of one unit of whole blood has been conveyed from the blood source to the separation chamber, the centrifuge mounting station and drive unit separate the whole blood in the separation chamber into plasma and red blood cells, and the pump station and the plurality of valves cooperate to convey separated plasma out of the separation chamber and into the plasma collection container, to convey separated red blood cells out of the separation chamber, and to convey additive solution out of the additive solution container, with the separated red blood cells and the additive solution being combined as a mixture and conveyed into the red blood cell collection container, execute a red blood cell recovery stage in which the pump station and the plurality of valves cooperate to convey air from the plasma collection container into the separation chamber to convey separated red blood cells out of the separation chamber and to convey additive solution out of the additive solution container, with the separated red blood cells and the additive solution continuing to be combined as the mixture and conveyed into the red blood cell collection container, execute an additive solution flush stage in which the pump station and the plurality of valves cooperate to convey additive solution from the additive solution container to the red blood cell collection container until a target amount of additive solution has been conveyed into the red blood cell collection container, and execute an air evacuation stage in which the pump station and the plurality of valves cooperate to convey air out of the red blood cell collection container.

7. The system of claim 6, wherein the fluid flow circuit includes a buffy coat collection container, the whole blood is separated into plasma, red blood cells, and a buffy coat between the separated plasma and the separated red blood cells within the processing chamber during the establish separation and collection stages, and the controller is configured to execute a buffy coat harvest stage after completion of the red blood cell recovery stage and before execution of the additive solution flush stage in which the pump station and the plurality of valves cooperate to convey air from the plasma collection container into the separation chamber to convey the buffy coat out of the separation chamber and into the buffy coat collection container.

8. The system of claim 6, wherein said plurality of containers includes a whole blood container containing one unit of whole blood, and the blood source is the whole blood container.

9. The system of claim 8, wherein the hardware component includes a pressure sensor configured to measure hydrostatic pressure of the whole blood container, and the controller is configured to end the collection stage based at least in part on the hydrostatic pressure of the whole blood container.

10. The system of claim 8, wherein the hardware component includes a first weight scale configured to measure a weight of the whole blood container, and the controller is configured to end the collection stage based at least in part on the weight of the whole blood container.

11. The system of claim 6, wherein the optical system is configured to determine a location of an interface between separated blood components within the separation chamber, and the controller is configured to end the establish separation stage when the optical system has determined that the interface is at a target location and when the controller has determined that steady state separation has been achieved.

12. The system of claim 6, wherein the fluid flow circuit includes a leukoreduction filter, the hardware component includes a pressure sensor configured to measure pressure of the leukoreduction filter, and the controller is configured to determine whether to control the pump station and the plurality of valves to direct the mixture to the red blood cell collection container with or without first passing through the leukoreduction filter based at least in part on the pressure of the leukoreduction filter.

13. The system of claim 12, wherein controller is configured to control the plurality of valves to direct the mixture through the leukoreduction filter at the beginning of the red blood cell recovery stage when the mixture is being directed through the leukoreduction filter at the end of the collection stage, and control the plurality of valves to direct the mixture to the red blood cell collection container without first passing through the leukoreduction filter during the red blood cell recovery stage when the mixture is being directed to the red blood cell collection container without first passing through the leukoreduction filter at the end of the collection stage.

14. The system of claim 1, wherein the controller is configured to actuate the pump station to convey blood from a blood source into the centrifuge mounting station and drive unit, actuate the centrifuge mounting station and drive unit to separate the blood in the centrifuge mounting station and drive unit into plasma, red blood cells, and a buffy coat between the separated plasma and the separated red blood cells, actuate the pump station to convey the separated plasma and the separated red blood cells out of the centrifuge mounting station and drive unit, and actuate the pump station to convey air into the centrifuge mounting station and drive unit to convey the buffy coat out of the centrifuge mounting station and drive unit for collection.

15. The system of claim 14, wherein said plurality of containers includes a plasma collection container, the controller is configured to actuate the pump station to convey air in the fluid flow circuit into the plasma collection container prior to actuating the centrifuge mounting station and drive unit to separate the blood in the centrifuge mounting station and drive unit, and the controller is configured to actuate the pump station to convey at least a portion of the air in the plasma collection container into the centrifuge mounting station and drive unit to convey the buffy coat out of the centrifuge mounting station and drive unit for collection.

16. The system of claim 1, wherein said plurality of containers includes a buffy coat collection container, and the controller is configured to actuate the pump station to convey blood from a blood source into the separation chamber, actuate the centrifuge mounting station and drive unit to separate the blood in the separation chamber into plasma, red blood cells, and a buffy coat between the separated plasma and the separated red blood cells, actuate the pump station to convey the separated plasma and the separated red blood cells out of the separation chamber, and actuate the pump station to convey air into the separation chamber to convey the buffy coat out of the separation chamber and into the buffy coat collection container.

17. The system of claim 16, wherein the separated plasma is conveyed out of the separation chamber via a plasma outlet port, the separated red blood cells are conveyed out of the separation chamber via a red blood cell outlet port, the air is conveyed into the separation chamber via the plasma outlet port, and the buffy coat is conveyed out of the separation chamber via the red blood cell outlet port.

18. The system of claim 1, wherein said plurality of containers includes a red blood cell source container, a washed red blood cell container, and a waste container, and the controller is configured to execute a priming stage in which the pump station and the plurality of valves cooperate to convey air within the fluid flow circuit into the waste container, execute a washing stage in which the pump station and the plurality of valves cooperate to convey red blood cells from the red blood cell source container to the separation chamber, the centrifuge mounting station and drive unit separate the red blood cells into a supernatant and washed red blood cells, and the pump station and the plurality valves cooperate to convey the supernatant out of the separation chamber and into the waste container and to convey the washed red blood cells out of the separation chamber and into the washed red blood cell container, execute a red blood cell recovery stage in which the pump station and the plurality of valves cooperate to convey air from the waste container into the separation chamber to convey washed red blood cells out of the separation chamber and into the washed red blood cell container, and execute an air evacuation stage in which the pump station and the plurality of valves cooperate to convey air out of the washed red blood cell container.

19. The system of claim 18, wherein said plurality of containers includes a wash solution container, and the controller is configured to execute a dilution stage in which the pump station and the plurality of valves cooperate to convey wash solution from the wash solution container to the washed red blood cell container until a target amount of wash solution has been conveyed into the washed red blood cell container.

* * * * *